(12) United States Patent
Modell et al.

(10) Patent No.: US 8,803,962 B2
(45) Date of Patent: Aug. 12, 2014

(54) SYSTEM AND METHOD FOR IMAGING DURING A MEDICAL PROCEDURE

(75) Inventors: Mark Modell, Natick, MA (US); Jason Sproul, Watertown, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 590 days.

(21) Appl. No.: 12/884,913

(22) Filed: Sep. 17, 2010

(65) Prior Publication Data

US 2011/0074943 A1 Mar. 31, 2011

Related U.S. Application Data

(60) Provisional application No. 61/247,008, filed on Sep. 30, 2009.

(51) Int. Cl.
*H04N 7/18* (2006.01)
(52) U.S. Cl.
USPC .......... 348/77; 348/143; 348/65; 348/333.01; 348/68; 348/74; 348/164; 348/E07.085
(58) Field of Classification Search
USPC .......... 348/77, 222.1, 750; 358/484; 600/110, 600/160; 345/589
IPC ......................................................... A61B 1/04
See application file for complete search history.

(56) References Cited

U.S. PATENT DOCUMENTS

| | | | |
|---|---|---|---|
| 7,268,924 B2 * | 9/2007 | Hussey et al. | 358/484 |
| 8,237,730 B1 * | 8/2012 | Anderson et al. | 345/589 |
| 2008/0094482 A1 * | 4/2008 | Yoshimura | 348/222.1 |
| 2008/0255416 A1 * | 10/2008 | Gilboa | 600/110 |
| 2009/0147154 A1 * | 6/2009 | Arai et al. | 348/750 |
| 2009/0156900 A1 * | 6/2009 | Robertson | 600/160 |

FOREIGN PATENT DOCUMENTS

| | | |
|---|---|---|
| JP | 10-305010 | 11/1988 |
| JP | 03-060627 | 3/1991 |
| JP | 07-023265 | 1/1995 |
| JP | 10-305010 | * 11/1998 |
| JP | 2004-229698 | 8/2004 |
| JP | 2007-336314 | 12/2007 |

OTHER PUBLICATIONS

International Search Report and Written Opinion mailed on Jan. 17, 2011, in corresponding International Application PCT/US2010/050148 (15 pages).
Office Action from the Japanese Patent Office in corresponding Japanese Application No. 2012-532209, dated Jan. 23, 2014.

* cited by examiner

*Primary Examiner* — Thao X Le
*Assistant Examiner* — Long Le
(74) *Attorney, Agent, or Firm* — Bookoff McAndrews, PLLC

(57) ABSTRACT

In one embodiment, an apparatus may include an imager configured to generate a plurality of frames at a frame frequency greater than an electromagnetic energy emission pulse frequency of a medical device, wherein each frame of the plurality of frames may include a first plurality of rows. The apparatus may also include an electronic shutter module configured to offset a start time of each row of the first plurality of rows in each frame from the plurality of frames from a start time of an adjacent row in that same frame. The apparatus may further include an image processing module configured to generate a plurality of valid frames based on at least a portion of the plurality of frames, wherein the plurality of valid frames may include a frame frequency lower than the frame frequency of the plurality of frames.

20 Claims, 14 Drawing Sheets

SYSTEM AND METHOD FOR IMAGING DURING A MEDICAL PROCEDURE

CROSS REFERENCE TO RELATED APPLICATION

This patent application claims the benefit of priority under 35 U.S.C. §§119 and 120 to U.S. Provisional Patent Application No. 61/247,008, filed Sep. 30, 2009, which is herein incorporated by reference in its entirety.

FIELD OF THE DISCLOSURE

Embodiments of the invention relate generally to medical devices and more particularly to imaging devices and methods for using such devices.

BACKGROUND OF THE DISCLOSURE

By using an imaging system to monitor a medical procedure, a medical practitioner can more accurately determine and control the progress of the procedure through visual inspection of the area of treatment. In non-invasive procedures, for example, an imaging endoscope enables the medical practitioner to examine the area of treatment while the medical procedure is in progress. For instance, during lithotripsy, a non-invasive procedure for the treatment of stones that typically form in the kidney, bladder, ureters, or gallbladder, a medical device (e.g., a lithotriptor) is used to provide pulses of focused, high-intensity shock waves (e.g., pressure waves) and/or electromagnetic radiation (e.g., laser) to break up the stones. By using an imaging endoscope within the medical device, a medical practitioner can locate the stones and aim or target the treatment effectively at the place where the stones are located. Moreover, the medical practitioner can monitor the progress of the stone fragmentation and adjust the procedure (e.g., intensity, frequency) accordingly.

The intense pulses produced by the medical device, however, can affect the operation of an imaging sensor in the imaging endoscope. For example, when sufficient back-scattered energy (e.g., electromagnetic radiation) strikes the imaging sensor during treatment, the timing of certain circuitry within the imaging sensor can be disrupted, affecting the quality of the video output. Moreover, back-scattered energy can saturate many of the sensing elements (e.g., pixels) in the imaging sensor, which also affects the quality of the video output. A reduced video output quality can limit the ability of the medical practitioner to effectively locate and/or treat the stones.

Thus, a need exists for an imaging system that can be used in medical procedures and that reduces and/or offsets the effects of energy pulses on the quality of the video output.

SUMMARY OF THE DISCLOSURE

One exemplary aspect of the present disclosure is directed to an apparatus. The apparatus may include an imager configured to generate a plurality of frames at a frame frequency greater than an electromagnetic energy emission pulse frequency of a medical device, wherein each frame of the plurality of frames may include a first plurality of rows. The apparatus may also include an electronic shutter module configured to offset a start time of each row of the first plurality of rows in each frame from the plurality of frames from a start time of an adjacent row in that same frame. The apparatus may further include an image processing module configured to generate a plurality of valid frames based on at least a portion of the plurality of frames, wherein the plurality of valid frames may include a frame frequency lower than the frame frequency of the plurality of frames.

Various embodiments of the disclosure may include one or more of the following aspects: the electronic shutter module may terminate a current frame from the plurality of frames in response to at least one of a synchronization pulse from the medical device and an electromagnetic energy associated with the medical device; the imager may be a solid-state imager having an addressable pixel array including a second plurality of rows, each row of the second plurality of rows may be associated with a row from the first plurality of rows in a frame from the plurality of frames; a valid portion of a frame from the plurality of frames may include at least one valid row and may be included in a valid frame from the plurality of valid frames; the image processing module may include a temporal filter configured to combine a valid portion of at least two adjacent frames from the plurality of frames to produce a valid frame from the plurality of valid frames; the imager may be configured to read out an initial frame from the plurality of frames in response to at least one of a power-on reset being complete and a synchronization signal from the medical device; a first frame from the plurality of frames may be before a second frame from the plurality of frames, and wherein the electronic shutter module may be configured to reset to a start of the second frame after the first frame is terminated in response to at least one of a synchronization pulse from the medical device and an electromagnetic energy associated with the medical device; a valid frame from the plurality of valid frames may include at least one valid row, the at least one valid row may have a number of valid pixels above a predetermined threshold number; a first frame from the plurality of frames may be before a second frame from the plurality of frames, and wherein the image processing module may be configured to replace an invalid portion of the second frame with an associated valid portion from the first frame; the image processing module may include a buffer configured to store a valid portion of at least one frame from the plurality of frames; the image processing module may be configured to adjust an illumination value associated with a pixel in a valid frame from the plurality of valid frames based on at least one of a dark reference pixel information received from the imager and a calibration information stored in the image processing module; the image processing module may include a temporal low-pass filter module configured to produce an output based on a dark reference pixel information received from the imager, and wherein the image processing module may be configured to adjust an illumination value associated with a pixel in a valid frame from the plurality of valid frames based on the output from the temporal low-pass filter; the image processing module may include a fast-settling filter module configured to produce an output based on a dark reference pixel information received from the imager, wherein the fast-settling filter module may be actuated in response to at least one of a synchronization pulse from the medical device and an electromagnetic energy associated with the medical device, and wherein the image processing module may be configured to adjust an illumination value associated with a pixel in a valid frame from the plurality of valid frames based on the output from the fast-settling filter; and the apparatus may include an endoscope.

Another exemplary aspect of the present disclosure is directed to a method. The method may include defining a plurality of video frames at an imager based on a received electromagnetic energy, wherein the imager may be operatively coupled to an image processing module. The method may also include determining whether a row in a video frame from the plurality of video frames is an invalid row in response to the received electromagnetic energy, wherein a first video frame from the plurality of video frames may be before a second video frame from the plurality of video frames. The method may further include replacing at least one invalid row in the second video frame with an associated valid row from the first video frame to produce a first valid video frame. The method additionally may include generating a plurality of valid video frames, wherein the plurality of valid video frames may include a frame frequency lower than a frame frequency of the plurality of video frames.

Various embodiments of the disclosure may include one or more of the following aspects: generating the plurality of video frames at a first frequency, the first frequency being greater than an electromagnetic energy emission pulse frequency of a medical device; a row in the second video frame may be invalid when an associated row in the first video frame is invalid and a number of valid pixels in the row in the second video frame may be below a predetermined threshold number; and deeming an invalid row to be a valid row after the invalid row has been replaced in a predetermined number of consecutive video frames from the plurality of video frames.

Yet another exemplary aspect of the present disclosure is directed to another method. The method may include inserting an imager into a body of a patient, activating a medical device to transmit an electromagnetic energy to the body of the patient, and generating a plurality of frames at a frame frequency greater than an electromagnetic energy emission pulse frequency of the medical device, wherein the imager may be configured to terminate at least a frame from the plurality of frames in response to at least one of a synchronization pulse from the medical device and an electromagnetic energy associated with the medical device. The method may also include offsetting a start time of each row in each frame from the plurality of frames from a start time of an adjacent row in that same frame.

Various embodiments of the disclosure may include one or more of the following aspects: adjusting a power level of the electromagnetic energy transmitted to the body of the patient from the medical device; adjusting the frame frequency of the plurality of frames; determining whether a frame from the plurality of frames is a first valid frame; and generating a plurality of valid frames including the first valid frame, the plurality of valid frames having a frame frequency lower than a frame frequency of the plurality of frames.

In this respect, before explaining at least one embodiment of the present disclosure in detail, it is to be understood that the present disclosure is not limited in its application to the details of construction and to the arrangements of the components set forth in the following description or illustrated in the drawings. The present disclosure is capable of embodiments in addition to those described and of being practiced and carried out in various ways. Also, it is to be understood that the phraseology and terminology employed herein, as well as the abstract, are for the purpose of description and should not be regarded as limiting.

The accompanying drawings illustrate certain exemplary embodiments of the present disclosure, and together with the description, serve to explain the principles of the present disclosure.

As such, those skilled in the art will appreciate that the conception upon which this disclosure is based may readily be used as a basis for designing other structures, methods, and systems for carrying out the several purposes of the present disclosure. It is important, therefore, to recognize that the claims should be regarded as including such equivalent constructions insofar as they do not depart from the spirit and scope of the present disclosure.

DETAILED DESCRIPTION

Figure 1:
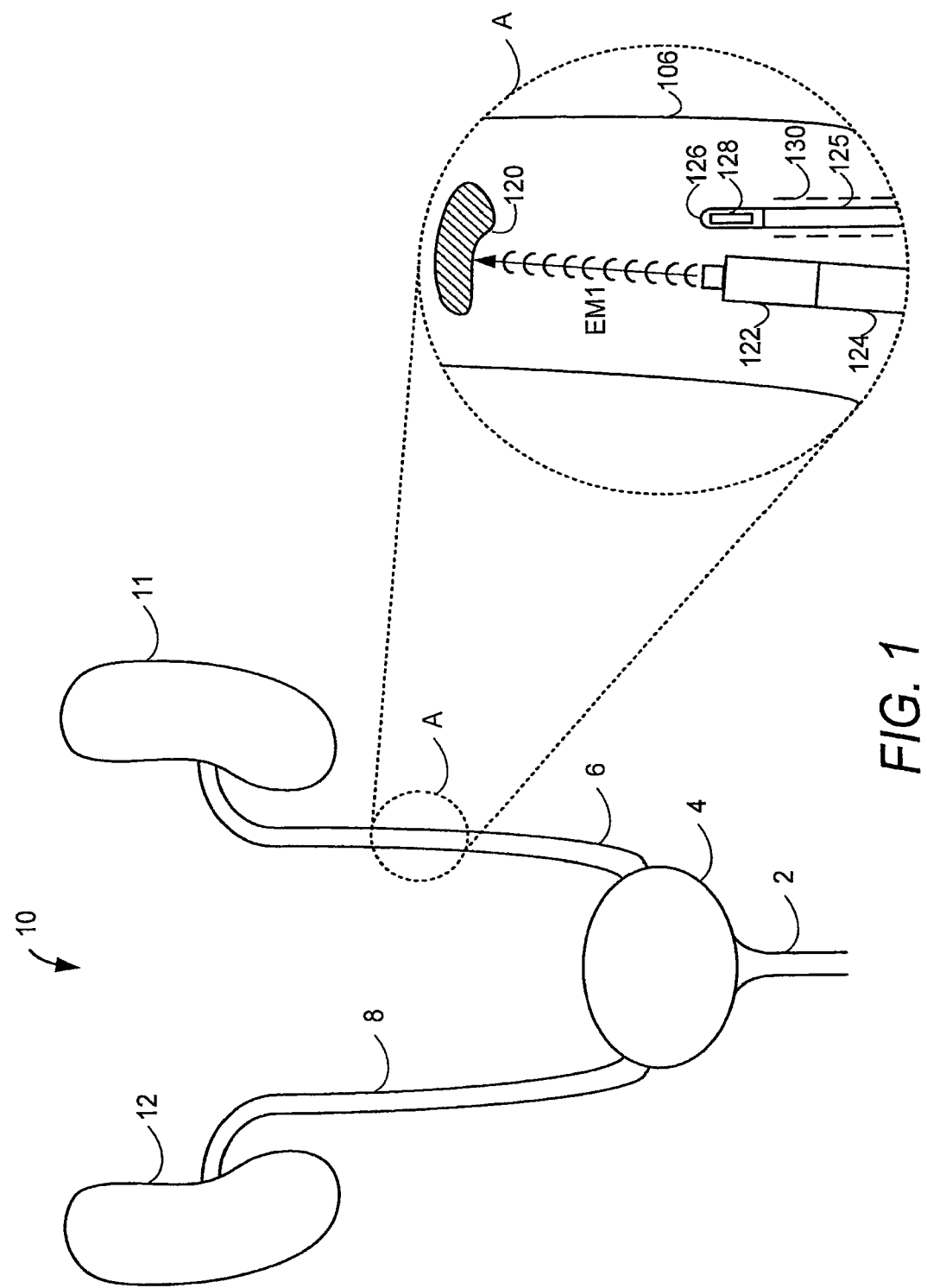
FIG. 1 is an illustration of a medical device and imaging device with a urinary system, according to an embodiment.

The devices and methods described herein are generally related to the use of an imaging system (e.g., imaging endoscope) within the body of a patient. For example, the devices and methods are suitable for use in a medical procedure such as lithotripsy, which is a non-invasive procedure for the treatment of kidney stones (i.e., urinary calculi) and stones of the gallbladder or the liver (i.e., biliary calculi). Lithotripsy is typically performed to remove the stones, prevent infection, and/or reduce the likelihood of recurrence in the patient. A lithotriptor is a medical device used during lithotripsy to break up the stones by using focused, high-intensity pressure (e.g., acoustic) or electromagnetic radiation (e.g., laser) pulses that minimize collateral tissue damage. The imaging system can be used to locate the stone and to appropriately target the treatment such that the pulses are aimed at the place where the stone is located. The treatment typically starts at a low power level, with long gaps between pulses to get the patient used to the sensation associated with the treatment. The frequency of the pulses and the power level can be gradually increased when appropriate to break up the stone more effectively. The stones break up into smaller pieces by shearing forces and/or cavitation bubbles surrounding the stone produced by the pressure and/or radiation pulses. The smaller pieces can be removed (e.g., via an endoscope) or can be passed through the patient's urinary system or through a cystic duct, for example. In some embodiments, the pulse frequency can be referred to as an energy frequency or as an electromagnetic energy emission frequency if the pulse frequency is related to the transmission (e.g., emission) of electromagnetic radiation.

Different types of lithotripsy procedures are available, including ultrasonic lithotripsy, extra corporal shock wave lithotripsy (ESWL), electrohydraulic lithotripsy (EHL), and urethroscopic stone removal, for example. Selection of any one of these lithotripsy procedures can depend on the type, size, number, and location of the stones, and/or on the condition of the patient. During ultrasonic lithotripsy, high-frequency sound waves are sent to the stone through an electronic probe inserted into the ureter. The stone fragments are typically passed by the patient or are removed surgically. In ESWL, pressure waves are sent from outside the patient's body and are highly focused on the stones to fragment the stones until they are reduced to small pieces or granules that can be passed in the patient's urine. For larger stones, multiple ESWL treatments may be required to reduce the stone to granules of an appropriate size. During EHL, a flexible probe is used to generate shock waves from an electrical source. The probe is positioned close to the stone through a flexible endoscope (e.g., a urethroscope). The shock waves are used to reduce the stone to small fragments that can be extracted using the endoscope or that can be passed by the patient. Urethroscopic stone removal is typically used to treat stones located in the middle and lower ureter. In this procedure, a urethroscope is passed through the urethra and bladder and into the ureter. Smaller stones are physically removed while larger stones are fragmented using electromagnetic radiation (e.g., laser).

An imaging system as described herein can be used to produce a video output that can assist a medical practitioner in performing and/or monitoring a medical procedure such as lithotripsy, for example. In this regard, the video output from the imaging system can allow the medical practitioner to locate stones, focus the shock waves or laser radiation at the precise place where the stones are located, and/or monitor the fragmentation and/or removal of the stones. The medical practitioner can adjust the target location of the lithotriptor pulses, the power level of the lithotriptor pulses, and/or the frequency of the lithotriptor pulses in accordance with the real-time feedback provided by the video output. The imaging system can include an imaging device or sensor and an image processing module. An electrical conduit can be used to connect the imaging device and the image processing module. One end of the electrical conduit can be coupled to the image processing module while the other end of the electrical conduit, the distal end portion, can be coupled to the imaging device and can be inserted into the patient's body.

It is noted that, as used in this written description and the appended claims, the singular forms "a," "an," and "the" include plural referents unless the context clearly dictates otherwise. Thus, for example, the term "a wavelength" is intended to mean a single wavelength or a combination of wavelengths. Furthermore, the words "proximal" and "distal" refer to direction closer to and away from, respectively, an operator (e.g., medical practitioner, medical practitioner, nurse, technician, etc.) who would insert the medical device into the patient, with the tip-end (i.e., distal end) of the device inserted inside a patient's body. Thus, for example, the end inserted inside a patient's body would be the distal end of an endoscope, while the end outside a patient's body would be the proximal end of the endoscope.

FIG. 1 is an illustration of a medical device and imaging device with a urinary system 10, according to an embodiment. The urinary system 10 has a urethra 2, a bladder 4, two ureters 6 and 8, and two kidneys 11 and 12. The kidneys 11 and 12 are bean-shaped organs that remove urea from the blood and produce mine from the urea, water, and other waste substances. Urine travels from the kidneys 11 and 12 down to the bladder 4 via the ureters 6 and 8, respectively. Each of the ureters 6 and 8 is a narrow conduit, typically about 8 to 10 inches in length. Muscles in the ureter walls regularly tighten and relax to force urine away from the kidneys 11 and 12 and into the bladder 4. The bladder 4 is a balloon-shaped hollow organ that stores the urine until the body is ready to empty the urine through the urethra 2.

Stones are typically formed in the kidney. The stones can remain in the kidney or can travel and be found anywhere in the urinary system 10. For example, stones can travel down from the kidney 11 to the ureter 6, which can result in a blockage at the ureter 6 that reduces or prevents the passage of urine from the kidney 11 to the bladder 4. If urine does not properly flow from the kidney 11 to the bladder 4 (e.g., stands still or backs up), a kidney infection can develop. In this regard, a medical procedure, such as lithotripsy, can be used to remove the stone from the ureter 6 and prevent further injury or illness to the patient.

FIG. 1 also shows an expanded view A of an inner portion of the uterer 6 that illustrates a medical device (e.g., a lithotripsy device) and imaging device associated with the presence of a stone 120 lodged within the ureter 6. During a urethroscopic stone removal procedure to remove the stone 120, for example, a medical device 124 and an endoscope 125 are passed through the urethra 2 and the bladder 4 and are positioned within the ureter 6 near the stone 120. The endoscope 125 includes a conduit 130 and a conduit distal end portion 126 having an imaging device or sensor 128. The medical device 124 includes a distal end portion 122 configured to produce an output EM1 having one or more pulses of electromagnetic radiation (e.g., laser radiation) and/or synchronization pulses. The output EM1 can be associated with multiple wavelengths (e.g., optical wavelengths), multiple power levels, and/or multiple pulse frequencies. In some embodiments, the pulses of electromagnetic radiation and/or synchronization pulses associated with the output EM1 can be generated by an electromagnetic radiation emission source (e.g., a laser source) (not shown) coupled to the distal end portion 122 of the medical device 124 via an optical fiber (not shown), for example. In some embodiments, one or more components and/or functions of the medical device 124 can be associated with (e.g., coupled to, included in) the endoscope 125 (or other imaging system that includes in the endoscope 125), or vice versa. For example, the electromagnetic radiation emission source (and/or one or more functions of the electromagnetic radiation source) can be coupled to or included in the endoscope 125.

The endoscope 125 enables the medical practitioner to position the imaging device 128 in the conduit distal end portion 126 near the area of treatment (i.e., the location of the stone 120) such that the medical practitioner can locate the stone 120 and/or to monitor the medical procedure. In some embodiments, the conduit distal end portion 126 can have an illumination device (not shown), such as a light emitting diode (LED), for example, to illuminate the area of treatment and provide a better video output for use by the medical practitioner. Once the area of treatment is located, the medical device 124 can be appropriately aimed at the area of treatment and the medical practitioner can adjust the power level and/or pulse frequency associated with the output EM1 to effectively fragment the stone 120. In some embodiments, the fragments of the stone 120 can be extracted using an endoscope (e.g., the endoscope 125) or can be passed by the patient. The endoscope 125 can be used in other medical procedures in addition to the urethroscopic stone removal procedure described above.

Figure 2:
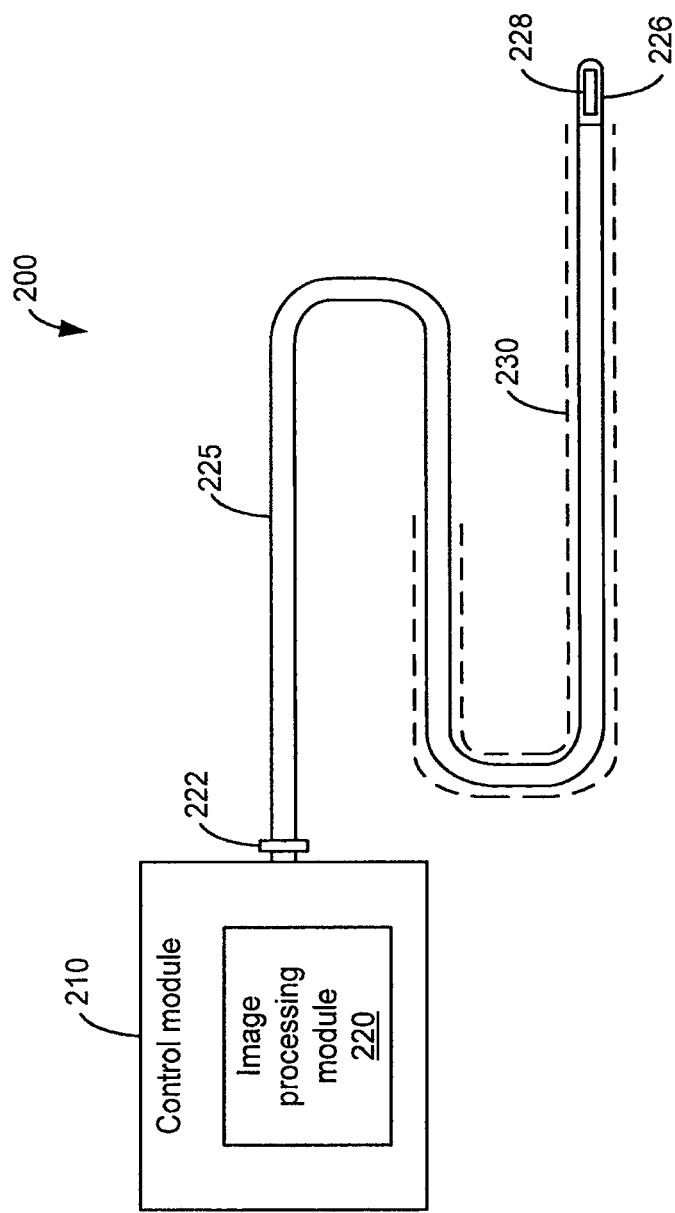
FIG. 2 is a schematic block diagram of an imaging system, according to an embodiment.

FIG. 2 is a schematic block diagram of an imaging system 200, according to an embodiment. The imaging system 200 includes a control module 210, a connector 222, a conduit 230, and a suitable catheter or endoscope 225. The imaging system 200 can be used in connection with a medical procedure, such as lithotripsy, for example. The conduit 230 includes a conduit distal end portion 226 having an imaging device or sensor 228. The control module 210 includes an image processing module 220.

The image processing module 220 is configured to process one or more outputs (e.g., video outputs) produced by the imaging device 228 and received by the control module 210 through the conduit 230. The image processing module 220 can be software-based (e.g., set of instructions executable at a processor, software code) and/or hardware-based (e.g., circuit system, processor, application-specific integrated circuit (ASIC), field programmable gate array (FPGA)).

In some embodiments, the control module 210 can be configured to provide power and/or control signals to one or more components in the conduit distal end portion 226 through the conduit 230. For example, the control module 210 can provide power and/or control signals to operate the imaging device 228. In another example, the control module 210 can provide power and/or control signals to operate an illumination device (not shown) in the conduit distal end portion 226. The control module 210 can provide power and/or control signals to one or more components in the conduit distal end portion 226 through, for example, the image processing module 220. In some embodiments, the control module 210 can include a laser source (not shown), such as a laser diode, for example, configured to produce an electromagnetic radiation output that can be coupled to the conduit distal end portion 226 through the conduit 230. The electromagnetic radiation output produced by the laser source can be emitted from the conduit distal end portion 226 to illuminate the area of treatment.

In some embodiments, the control module 210 can include additional components (not shown) configured to provide additional processing capabilities. For example, the control module 210 can include one or more modules configured to perform color processing operations. In another example, the control module 210 can include one or more modules configured to perform video encoding or compression operations. In another example, the control module 210 can include one or more modules configured to format video into one or more recording formats and/or video transmission formats such as the National Television System Committee (NTSC), high-definition video formats, and standard-definition video formats. In some embodiments, at least some of the additional processing capabilities described above with respect to the control module 210 can be performed by the image processing module 220.

The conduit 230 is coupled to the control module 210 through the connector 222. The proximal end portion of the conduit 230 is configured to receive power and/or control signals from the control module 210 and the distal end portion of the conduit 230 is configured to receive at least a video output from the imaging device 228 in the conduit distal end portion 226. The conduit 230 can include, for example, one or more electrically conductive wires, one or more optical fibers, and/or one or more coaxial cables. The conduit 230 includes an elongate portion that can be flexible to allow the elongate portion to be maneuvered within the endoscope 225, for example.

The endoscope 225 can define one or more lumens. In some embodiments, the endoscope 225 includes a single lumen that can receive therethrough various components such as the conduit 230. The endoscope 225 has a proximal end configured to receive the conduit distal end portion 226 and a distal end configured to be inserted into a patient's body for positioning the conduit distal end portion 226 in an appropriate location for a medical procedure. For example, during a lithotripsy procedure to remove stones in the urinary system 10 described above with respect to FIG. 1, the endoscope 225 can be used to place the conduit distal end portion 226 at or near the stone 120. The endoscope 225 includes an elongate portion that can be flexible to allow the elongate portion to be maneuvered within the body (e.g., urinary system 10). The endoscope 225 can also be configured to receive various medical devices or tools through one or more lumens of the endoscope, such as, for example, irrigation and/or suction devices, forceps, drills, snares, needles, etc. An example of such an endoscope with multiple lumens is described in U.S. Pat. No. 6,296,608 to Daniels et al., the disclosure of which is incorporated herein by reference in its entirety. In some embodiments, a fluid channel (not shown) is defined by the endoscope 225 and coupled at a proximal end to a fluid source (not shown). The fluid channel can be used to irrigate an interior of the patient's body during a medical procedure. In some embodiments, a different channel (not shown) is defined by the endoscope 225 and coupled at the proximal end to a suction source (not shown). The channel can be used to remove stone fragments that result from lithotripsy, for example.

Figure 3:
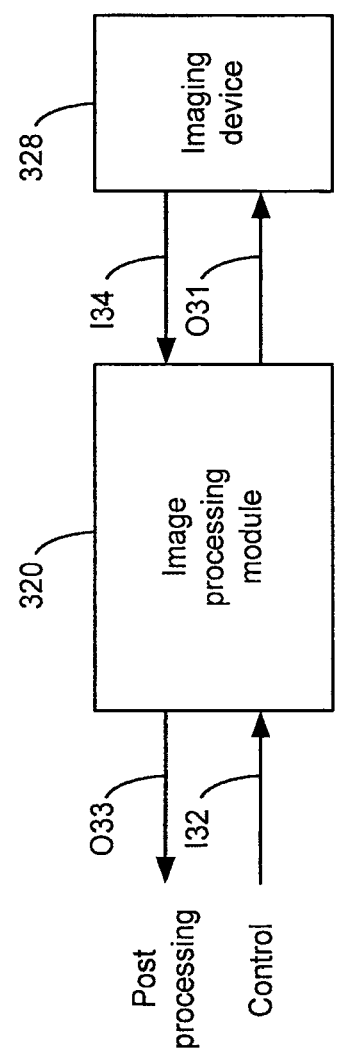
FIG. 3 is a schematic block diagram of an image processing module and an imaging device, according to an embodiment.

FIG. 3 is a schematic block diagram of an image processing module 320 and an imaging device 328, according to an embodiment. The image processing module 320 and/or the imaging device 328 can be used in the imaging system 200 described above with respect to FIG. 2. The image processing module 320 is configured to perform various video processing operations including, for example, adjusting, replacing, and/or modifying invalid portions of one or more video frames received from a video output produced by the imaging device 328. In some embodiments, the imagining device 328 can be referred to as an imager. The image processing module 320 is configured to adjust and/or modify a rate or frequency associated with the video frames processed by the image processing module 320. The functionality provided by the image processing module 320 can be software-based (e.g., set of instructions executable at a processor, software code) and/or hardware-based (e.g., circuit system, processor, application-specific integrated circuit (ASIC), field programmable gate array (FPGA)). In some embodiments, the image processing module 320, when associated with (e.g., coupled to, included in) an endoscope such as that shown in FIG. 2, can be referred to as an endoscopic image processing module. In some embodiments, the image device 328, when associated with (e.g., coupled to, included in) an endoscope such as that shown in FIG. 2, can be referred to as an endoscopic imager.

The image processing module 320 is configured to receive an input I32 that includes one or more signals to control the operation of the image processing module 320. The control signals associated with the input I32 can result from the operation of other components or modules in the control module 210 described above with respect to FIG. 2. For example, one or more control signals associated with the input I32 can be received from components or modules in the control module 210 in response to input received from a user (e.g., medical practitioner) in connection with a medical procedure. The input I32 includes one or more signals to control the adjustment, replacement (e.g., replacement timing), and/or modification of invalid portions of one or more video frames to be processed by the image processing module 320. The input I32 can include, for example, one or more signals to control a rate or frequency associated with video frames processed by the image processing module 320.

The input I32 can also include one or more signals that can be used by the image processing module 320 to control the operation of the imaging device 328. For example, the input I32 can include one or more signals that can be used by the image processing module 320 to control the rate or frequency associated with the video output of the imaging device 328. In this regard, the image processing module 320 is configured to produce an output O31 that includes one or more signals to control the operation of the imaging device 328. In some instances, the image processing module 320 can be configured to be a source of power (e.g., DC voltage) to the imaging device 328 via the output O31, or via a different output (not shown).

The imaging device 328 can be a complementary metal-oxide-semiconductor (CMOS) image sensor, a charge-coupled-device (CCD) image sensor, an infrared (IR) image sensor, a micro-electro-mechanical (MEM) array, or a focal plane array, for example. In one embodiment, the imaging device 328 is configured to receive electromagnetic radiation in the visible range (e.g., between about 400 nm and 800 nm) and/or near infrared range (e.g., between about 800 nm and 1200 nm) associated with a particular field of view (e.g., area of treatment). The imaging device 328 is configured produce one or more video frames, each video frame representative of a scene and a time associated with the field of view from which the electromagnetic radiation was received and based on the received electromagnetic radiation.

The image processing module 320 is configured to receive an input I34 from the imaging device 328 that includes one or more video frames (i.e., the video output). The video frames in the input I34 are processed by the image processing module 320. The image processing module 320 can be configured to operate with more than one type of imaging device 328 such as imaging devices having different resolutions and/or configured to capture a different spectrum of electromagnetic radiation.

The image processing module 320 is configured to produce an output O33 having a video stream that includes multiple frames processed by the image processing module 320. In some embodiments, the output O33 can be sent to another component or portion of the proximal end portion 210 described above with respect to FIG. 2, for example, for further processing (e.g., post-processing). The output O33 can include information related to the configuration and/or operation of the image processing module 320 and/or of the imaging device 328.

Figure 4:
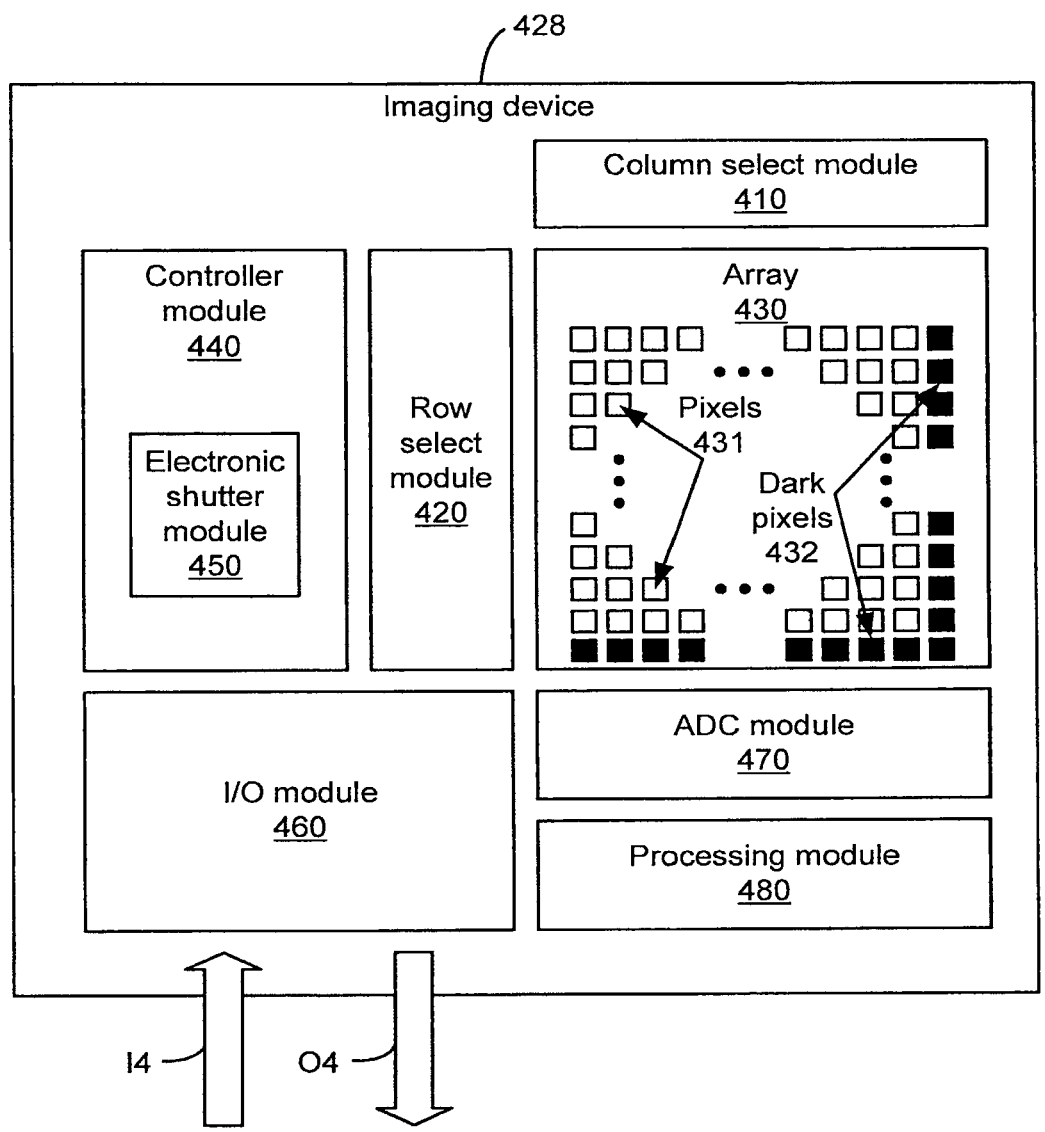
FIG. 4 is a schematic block diagram of an imaging device, according to an embodiment.

FIG. 4 is a system block diagram of an imaging device 428, according to an embodiment. The imaging device 428 includes a column select module 410, a row select module 420, an pixel array 430, a controller module 440, and an input/output (I/O) module 460. Optionally, the imaging device 428 can include an analog-to-digital converter (ADC) module 470 and/or a processing module 480. The controller module 440 includes an electronic shutter module 450. The functionality provided by the imaging device 428 is hardware-based or hardware-based and software-based.

The pixel array 430 includes multiple picture elements (i.e. pixels) 431 arranged in one or more columns and rows. For example, the pixel array 430 can have a Video Graphics Array (VGA) size or resolution that typically includes 640 columns by 480 rows of pixels 431. In other embodiments, the pixel array 430 can have an array size smaller than a VGA-sized array or can have an array size larger than a VGA-sized array. For example, the pixel array 430 can have a super VGA (SVGA) size that typically includes 800 columns by 600 rows of pixels 431. In another example, the pixel array 430 can have more than one million pixels 431 (e.g., megapixel array) arranged in multiple configurations of columns and rows. In some embodiments, the size of the pixel array 430 can be customized for a particular application (e.g., a particular medical procedure). In this regard, the size of the pixel array 430 may depend on a desirable resolution that is suitable for assisting a medical practitioner during a particular medical procedure.

Each pixel 431 in the pixel array 430 is configured to receive electromagnetic radiation (not shown) and convert the received electromagnetic radiation to an associated electrical charge or voltage (not shown). Pixels in the pixel array 430 can have an optical filter (not shown) to filter out or reflect portions of the electromagnetic spectrum incident upon the pixel such that the pixel produces an electrical charge associated only with the portion of the electromagnetic spectrum that passes through the optical filter. By using optical filters of different spectral characteristics throughout the pixel array 430 (e.g., repeated color filter mosaic pattern), the imaging device 428 can produce a video output having color information.

The pixel array 430 can include multiple dark (reference) pixels 432 associated with one or more columns and/or rows. The dark pixels 432 are covered (e.g., metal layer) such that electromagnetic radiation incident upon the dark pixels 432 is substantially reflected. The dark pixels 432 are configured to produce DC voltages and/or charges associated with certain operations of the pixel array 430 such that the DC voltages and/or charges produced by the dark pixels 432 can be used to offset and/or compensate for certain DC voltages and/or charges produced by pixels 431 during operation of the imaging device 428. In some embodiments, the information associated with the dark pixels 432 can determined the operation of the imaging device 428, during a manufacturing calibration operation, and/or during a post-manufacturing system calibration operation, for example. The information associated with the dark pixels 432 can be stored in the I/O module 460, the processing module 480, and/or in a buffer (not shown) or memory (not shown) in the imaging device 428. The dark pixels 432 can be located on the sides of the pixel array 430.

The I/O module 460 is configured to receive an input I4 from, for example, a given image processing module such as the image processing module 320 described above with respect to FIG. 3. The input I4 includes one or more signals and/or pulses associated with the operation of the imaging device 428. For example, the input I4 can include signals and/or pulses associated with the timing and/or frequency of operation of the imaging device 428 such as a clock signal, a trigger, a frequency control signal, a synchronization signal, a shutter control signal, and/or a reset. The I/O module 460 is configured to communicate or send signals and/or pulses received via the input I4 to one or more components of the imaging device 428.

In some embodiments, the input I4 can include signals and/or pulses (e.g., synchronization pulse) associated with the operation of a medical device such as a lithotriptor, for example. When a processing module 480 is included in the imaging device 428, the input I4 can include signals and/or pulses associated with the operation of the processing module 480. For example, the input I4 can include signals and/or pulses associated with controlling a format of a video output produced by the processing module 480.

The I/O module 460 is configured to produce an output O4 that includes one or more signals and/or pulses associated with a video output or video stream produced by the imaging device 428. The video output or video stream can include one or more video frames and/or portions of video frames. The output O4 can be sent to, for example, a given image processing module such as the image processing module 320 described above with respect to FIG. 3. The output O4 can be sent to other components such as video cards (not shown) or frame grabbers (not shown). A video card or a frame grabber is an electronic device configured to receive an analog video signal or a digital video stream. A frame grabber, for example, can be used in an imaging or vision system to store, display, and/or transmit video content in raw (i.e., uncompressed) or compressed digital form.

The controller module 440 is configured to control the operation of at least some of the components of the imaging device 428. For example, the controller module 440 is configured to control timing of operations associated with the imaging device 428. In this regard, the electronic shutter module 450 is configured to control timing of operations associated with the column select module 410, the row select module 420, and the pixel array 430. For example, the controller module 440 is configured to control the time a given pixel 431 is collects a charge or voltage associated with the intensity and/or spectrum of the electromagnetic radiation incident on the pixel 431 (i.e., exposure or integration operation). The controller module 440 is configured to control which rows from the multiple rows in the pixel array 430 are to be integrated (i.e., collect charges resulting from the incident electromagnetic radiation) at a particular time. The charge or voltage associated with each pixel 431 is transferred to a storage element (e.g., a capacitor) coupled to the pixel to await a readout operation. The controller module 440 is configured to control the readout operation that follows the exposure or integration operation. In the readout operation, the charge or voltage produced by each pixel 431 during the exposure operation is transferred to the ADC module 470 for conversion to a digital value or number (e.g., 8-bit or 10-bit number) or is transferred out of the imaging device 428 via the output O4, for example.

The electronic shutter module 440 is configured to control operations of the imaging device 428 associated with a global shutter or a rolling shutter, for example. When the imaging device 428 is configured to operate with a global or synchronous shutter, the electronic shutter module 440 controls the rows in the pixel array 430 via the row select module 420 such that the pixels in each of the rows are reset (i.e., row reset) at the same time and are exposed for the same period of time (i.e., integration time). Because the rows are exposed concurrently, using a global shutter typically reduces jagged or blurred effects that occur during fast-moving or fast-changing scenes. The charge or voltage associated with each pixel 431 in a given row is transferred to a storage element (e.g., a capacitor) coupled to the pixel to await the readout operation. The electronic shutter module 440 controls the readout of the charge or voltage associated with each pixel 431 in a given row via the column select module 410. A video frame is built by reading out the exposed rows, one at a time, after the exposure operation is complete. The time it takes to readout the exposed rows that are used to build or compose a video frame can be reflected to as the readout time. The ADC module 470 and/or the I/O module 460 can include a buffer (not shown) or memory (not shown) configured to store at least a portion of a video frame. Once the rows have been read out and the video frame has been completed, the electronic shutter module 440 is configured to reset the pixel array 430 (i.e., frame reset) such that a new video frame can be built.

In this regard, the frequency or frame rate associated with the imaging device 428 is based at least partly on the time associated with the exposure operation (i.e., integration time) and the time associated with the readout operation (i.e., readout time). For example, the longer the integration time and the readout time associated with building a video frame from multiple exposed rows, the lower the frequency or frame rate at which the imaging device 428 can be operated.

When the imaging device 428 is configured to operate with a rolling shutter, the electronic shutter module 440 controls the rows in the pixel array 430 via the row select module 420 such that each row is reset (i.e., row reset) at a different time and then exposed for a period of time (i.e., integration time). For example, each row that is used to build a video frame can be reset or start integrating at a time that is offset from a rest or start time of an adjacent row in the same video frame. In some embodiments, sets of rows can have a reset or start time that is offset from a reset or start time of an adjacent set of rows in the same video frame. Because the rows are exposed in an offset manner, using a rolling shutter typically produces a uniformly exposed image even during fast-changing scenes. The charge or voltage associated with each pixel 431 in each exposed row is transferred to a storage element coupled to the pixel to await the readout operation. The electronic shutter module 440 controls the readout of the charge or voltage associated with the pixels 431 in a given row via the column select module 410. A video frame is built as each exposed row is read out following completion of the exposure of that row.

In some embodiments, circuitry within the electronic shutter module 450 can be affected by, for example, a synchronization pulse or an electromagnetic radiation (e.g., combustion flash) associated with the operation of a medical device such as a lithotriptor. The electronic shutter module 450 can disadvantageously reset (i.e., frame reset) from a video frame to a new video frame as a result of the operation of the medical device. Said differently, the electronic shutter module 450 can prematurely terminate a video frame and start a new video frame when a synchronization pulse or an electromagnetic radiation from a medical device occurs. In this regard, the operation of a medical device near the imaging device 428 can have an effect on the quality of the video output 'Of the imaging device 428 by disrupting the timing and/or control provided by the electronic shutter module 450, for example.

Figure 5A:
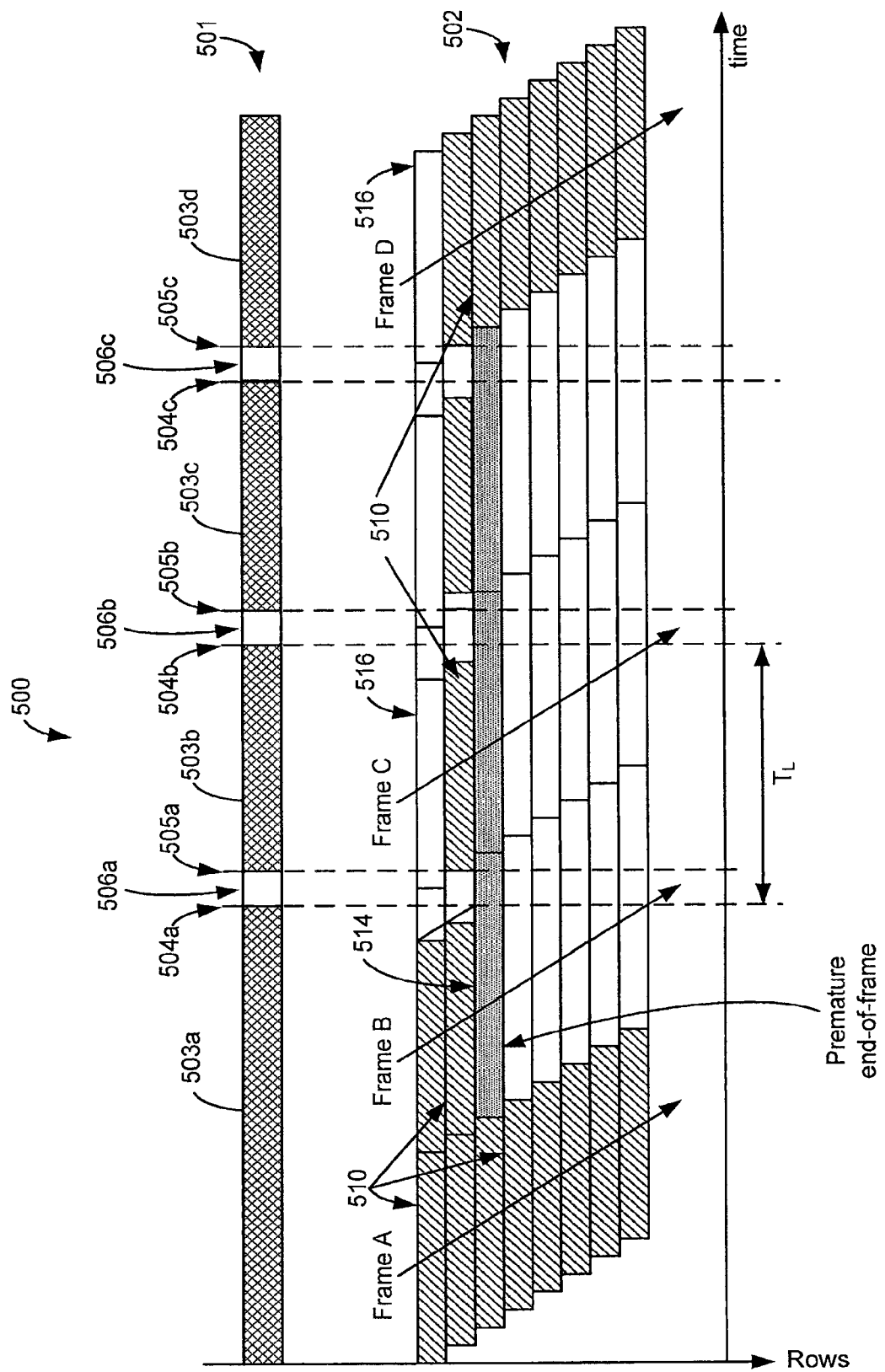
FIG. 5A is a timing diagram illustrating frame resetting on an imaging device resulting from the operation of a medical device.

FIG. 5A is a timing diagram 500 illustrating frame resetting on an imaging device that results from the operation of a medical device (e.g., a lithotriptor), according to an embodiment. The timing diagram 500 includes a top portion 501 that illustrates periods when synchronization or electromagnetic radiation pulses are delivered by a medical device such as the medical device 124 described above with respect to FIG. 1, for example. The timing diagram 500 includes a bottom portion 502 that illustrates multiple video frames associated with a video output from a given imaging device being used with the medical device in a medical procedure (e.g., a lithotripsy procedure), such as the imaging devices 228, 238, and 428 described above with respect to FIGS. 2-4, respectively, for example.

The top portion 501 of the timing diagram 500 includes time periods 503*a*, 503*b*, 503*c*, and 503*d* (shown with a hatched pattern) during which the medical device does not deliver an electromagnetic radiation pulse to the treatment area or sends a synchronization pulse to the imaging device. The time periods 506a, 506b, and 506c (shown with a white pattern) illustrate periods of time during which the medical device delivers an electromagnetic radiation pulse to the treatment area or sends a synchronization pulse. For example, the time instances 504a and 505a are associated with the start and end, respectively, of an electromagnetic radiation pulse delivered to the patient during time period 506a. A combustion flash can result when the electromagnetic radiation delivered to the area of treatment reaches the stone. The combustion flash can be received by the imaging device as a large pulse or blast of electromagnetic radiation, for example. A period $T_L$ between electromagnetic radiation and/or synchronization pulses is associated with the frequency of operation ($F_L$) of the medical device.

The bottom portion 502 of the timing diagram 500 illustrates an example of the effects of the medical device pulses on the video frames produced by the imaging device. In this example, the imaging device is operated using a rolling shutter such that each row in a video frame has an exposure start time (e.g., a row reset) that is offset from the exposure start time of an adjacent row in the same frame. Moreover, the frequency of operation of the imaging device (i.e., the frame rate) is substantially the same as the frequency of operation of the medical device ($F_L$).

FIG. 5A shows a frame A at the start (left) of the bottom portion 502 that includes multiple valid rows 510 (shown with a hashed pattern). A valid row 510 is a row that includes a number of valid pixels above a threshold number, for example, and that has not be prematurely terminated or corrupted as a result of a frame resetting that occurs from a synchronization pulse produced by the medical device or from receiving electromagnetic radiation associated with the medical device (e.g., a combustion flash) at the imaging device. A valid pixel can be, for example, a pixel that operates properly (e.g., not defective) and./or is not saturated from being exposed to very high levels of electromagnetic radiation. The frame A occurs within the time period 503a during which the medical device does not deliver electromagnetic radiation to the treatment area or sends a synchronization pulse.

A frame B is shown having its first and second top rows being valid rows 510. Both the first and second rows occur within the time period 503a during which the medical device does not deliver electromagnetic radiation to the treatment area or sends a synchronization pulse. The end portion of the third row (shown with a dotted pattern) of frame B, however, occurs within the time period 506a during which the medical device delivers electromagnetic radiation to the treatment area or sends a synchronization pulse to synchronize the imaging device and the medical device. In this example, the medical device pulse results in a frame reset at the imaging device (i.e., circuitry in the imaging device produces a frame reset) such that frame B is prematurely terminated (i.e., premature end-of-frame) at its third row. The third row of frame B is corrupted by the frame reset that occurs. A corrupt row 514 can be a row that includes a number invalid pixels resulting from a frame reset produced by a medical device pulse.

The imaging device starts a new frame C following the frame resetting that occurs as a result of the premature end of frame B. Frame C, however, has as its first rowan invalid row 516 (shown in white pattern). The first row of frame C starts when the medical device produces a pulse within the time period 506a. The first valid row 510 of frame C is its second row. As was shown with respect to frame B, the third row of frame C is corrupted by a frame resetting that occurs from a pulse produced by the medical device during the time period 506b such that frame C is prematurely terminated at its third row. FIG. 5A also shows a frame D having as its top rowan invalid row 516 that results from a pulse produced by the medical device during time period 506c. The remaining rows in frame D, however, are valid rows 510 as they occur within the time period 503d in which the medical device does not deliver an electromagnetic radiation pulse or sends a synchronization pulse.

The example described in FIG. 5A illustrates the effects of operating the medical device at substantially the same frequency as the frame rate of the imaging device. Multiple video frames, in some instances multiple consecutive video frames, can be prematurely terminated by the operation of the medical device. The terminated video frames may include few if any valid rows. In this regard, the quality of the video output can be severely affected by the effects that the pulses produced by the medical device have on the imaging device. As a result, a medical practitioner may not be able to use the video output produced by the imaging device to effectively assist in the performance of a medical procedure (e.g., a lithotripsy procedure).

Figure 5B:
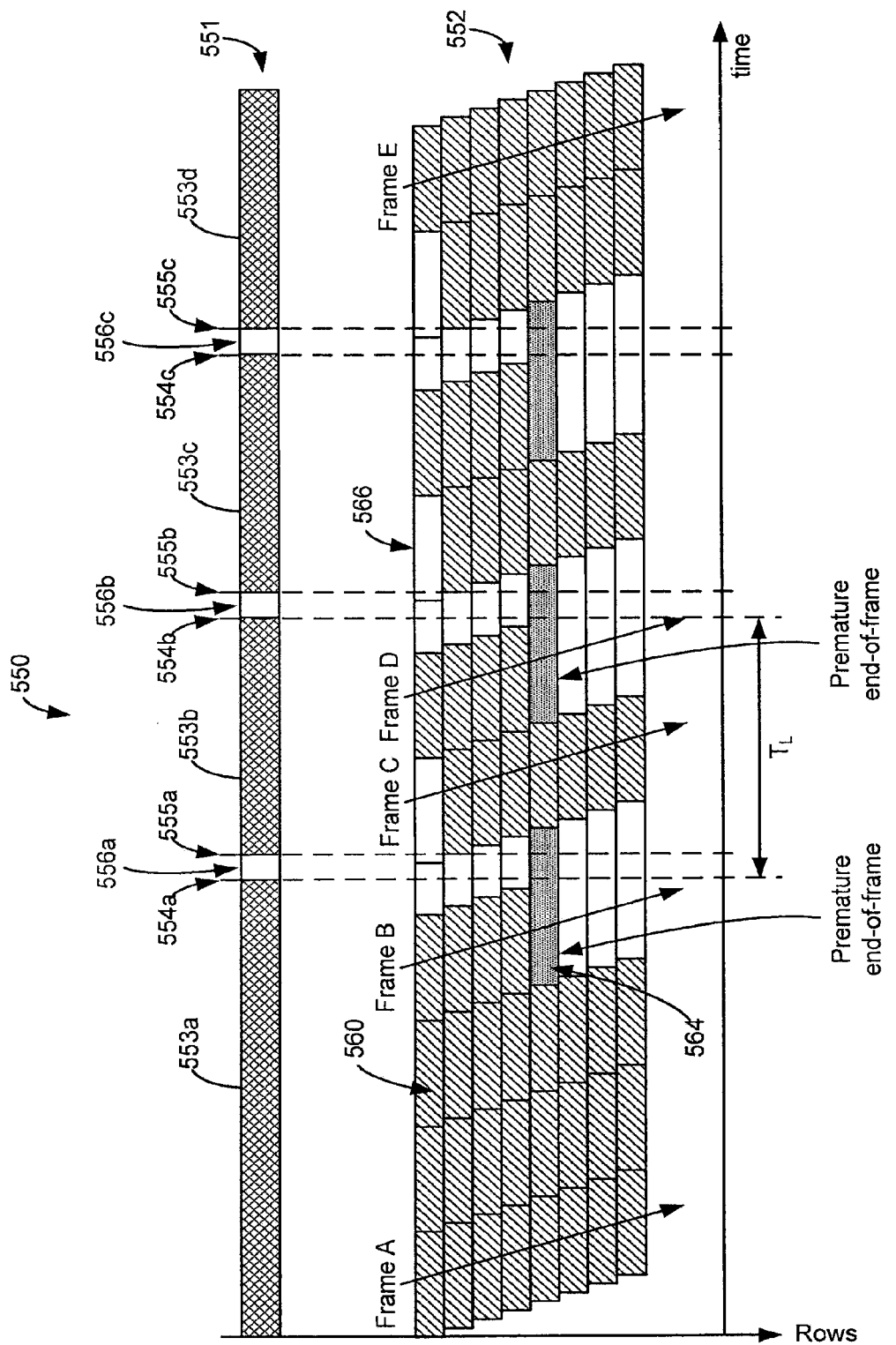
FIG. 5B is a timing diagram illustrating an increased number of valid rows when an imaging device is operated at twice the frequency of operation of a medical device, according to an embodiment.

FIG. 5B is a timing diagram 550 illustrating an increased number of valid rows when an imaging device is operated at, for example, twice (or higher) the frequency of operation of a medical device, according to an embodiment. The timing diagram 550 includes a top portion 551 that illustrates periods when electromagnetic radiation pulses are delivered or synchronization pulses are sent by a medical device, such as the medical device 124 described above with respect to FIG. 1, for example. The timing diagram 550 includes a bottom portion 552 that illustrates multiple frames associated with a video output from a given imaging device being used in the medical procedure (e.g., a lithotripsy procedure), such as the imaging devices 228, 238, and 428 described above with respect to FIGS. 2-4, respectively, for example. In this example, the imaging device operates at a frame rate having a frequency that is at least twice the frequency of operation the medical device. In some embodiments, the frame rate can be less than twice the frequency of the operation of the medical device (the pulse frequency).

The top portion 551 of the timing diagram 550 includes time periods 553a, 553b, 553c, and 553d (shown with a hatched pattern) during which the medical device does not deliver an electromagnetic radiation pulse to the treatment area or sends a synchronization pulse to the imaging device. The time periods 556a, 556b, and 556c (shown with a white pattern) illustrate periods of time during which the medical device delivers an electromagnetic radiation pulse to the treatment area or sends a synchronization pulse. For example, the time instances 554a and 555a are associated with the start and end, respectively, of an electromagnetic radiation pulse delivered to the patient during time period 556a. A period $T_L$ between electromagnetic radiation and/or synchronization pulses is associated with the frequency of operation ($F_L$) of the medical device and is substantially the same period as shown in FIG. 5A.

The bottom portion 552 of the timing diagram 550 illustrates an example of the effects of increasing the frame rate of the imaging device to a frequency of at least twice the frequency of operation (e.g., energy or pulse frequency) of the medical device. In this example, the imaging device is operated using a rolling shutter such that each row in a video frame has an exposure start time (e.g., a row reset) that is offset from the exposure start time of an adjacent row in the same video frame.

FIG. 5B shows a frame A at the start (left) of the bottom portion 552 that includes multiple valid rows 560 (shown with a hashed pattern). The frame A occurs within the time period 553a during which the medical device does not deliver electromagnetic radiation to the treatment area or sends a synchronization pulse. A frame B is shown having its top four rows being valid rows 560. The top four rows of frame B occur within the time period 553a during which the medical device does not deliver electromagnetic radiation to the treatment area or sends a synchronization pulse. The end portion of the fifth row (shown with a dotted pattern) of frame B, however, occurs within the time period 556a during which the medical device delivers electromagnetic radiation to the treatment area or sends a synchronization pulse to synchronize the imaging device and the medical device. In this example, the medical device pulse produces a frame reset such that frame B is prematurely terminated (i.e., premature end-of-frame) at its fifth row. The fifth row of frame B is corrupted by the frame reset that occurs and is shown as a corrupt row 564.

Because of the higher frame rate of the imaging device, a given video frame that occurs after the premature end of frame B is likely to have more valid rows than video frames that occur after a premature end of a frame when the frequency associated with the frame rate of the imaging device is substantially the same as the frequency of operation of the medical device. For example, a new frame C follows the frame resetting that occurs as a result of the premature end of frame B. Frame C, however, has as its top row an invalid row 566 (shown in white pattern) that starts when the medical device produces a pulse within the time period 556a. Although the top row of frame C is an invalid row 556, the remaining rows of frame C occur during the time period 553b and are valid rows 560. Following the last valid row 560 of frame C, a scheduled frame reset occurs and a new frame D starts during the time period 553b. Similar to frame B, the frame D ends prematurely at its fifth row from the top as a result of a pulse produced by the medical device during the time period 556b. A frame E is shown at the end (right) of the bottom portion 552 in which all the rows are valid rows 560.

When the imaging device is operated at twice (or higher) the frequency of operation of the medical device, it is possible to recover the image information with a small loss of signal-to-noise ratio. For example, in one embodiment, pairs of adjacent (or more than two) video frames (e.g., frame C and frame D in FIG. 5B) can be added, combined, etc. or at least the valid portions of pairs each adjacent video frame can be added, combined, etc. to substantially replicate the behavior of an imaging device operating at a lower frequency or frame rate. In another embodiment, depending on the amount of latency that may be accepted through the imaging system, more complex temporal filtering operations, such as a sin (x)/x filter, for example, can be used to combine the information in valid rows of adjacent video frames while minimizing temporal aliasing effects. Moreover, the increase in frame rate in the imaging device can reduce the apparent motion artifacts that are typically produced by a rolling shutter.

In some embodiments, frame processing techniques such as interpolation, extrapolation, frame delays, and/or so forth can be used to define valid frames (or portions of valid frames) when the frame rate of the imaging device is less than twice the frequency of operation of the medical device. Information associated with one or more frames can be, for example, interpolated to produce portions of (or entire) valid frames that will replace portions of (or entire) invalid frames. In some embodiments, the display of the frames (e.g., the valid frames) to an operator can be delayed (e.g., delayed a few frames) to allow for time to perform the interpolation. The duration of the delay can be defined so that the delay is substantially imperceptible to, for example, an operator.

In some embodiments, the imaging device (e.g., imaging sensor) can be configured such that a readout operation or process occurs upon the end of a power-on reset (POR) operation, or upon receiving a synchronization signal, such as a synchronization pulse from a medical device, for example. It may be desirable that the duration of the POR operation be short to guarantee that the internal states of certain components and/or portions of the imaging device are properly set. In some embodiments, at the end of the POR operation the imaging device can reset each of the rows and may not perform a readout operation until after a exposure or integration operation of the rows has occurred. By instead following the POR operation with a readout operation and having the reset of rows occur after the readout operation, it may be possible to have at least two complete (i.e., not prematurely terminated) video frames read out between medical device pulses such that the valid rows in each of the two complete video frames can be added or combined to produce a complete and valid video frame that can be presented to a medical practitioner.

As described above, in some instances, the electromagnetic radiation pulses produced by a medical device can result in combustion flashes. The light or flashes that result from the combustion (e.g., fragmentation) of the stone can saturate pixels in a given imaging device. A large number of saturated pixels can result in loss of image information in the video output from the imaging device. In these instances, the imaging device need not reset (e.g., frame reset) for the loss of information that results from pixel saturation to affect the quality of the video output.

Figure 6A:
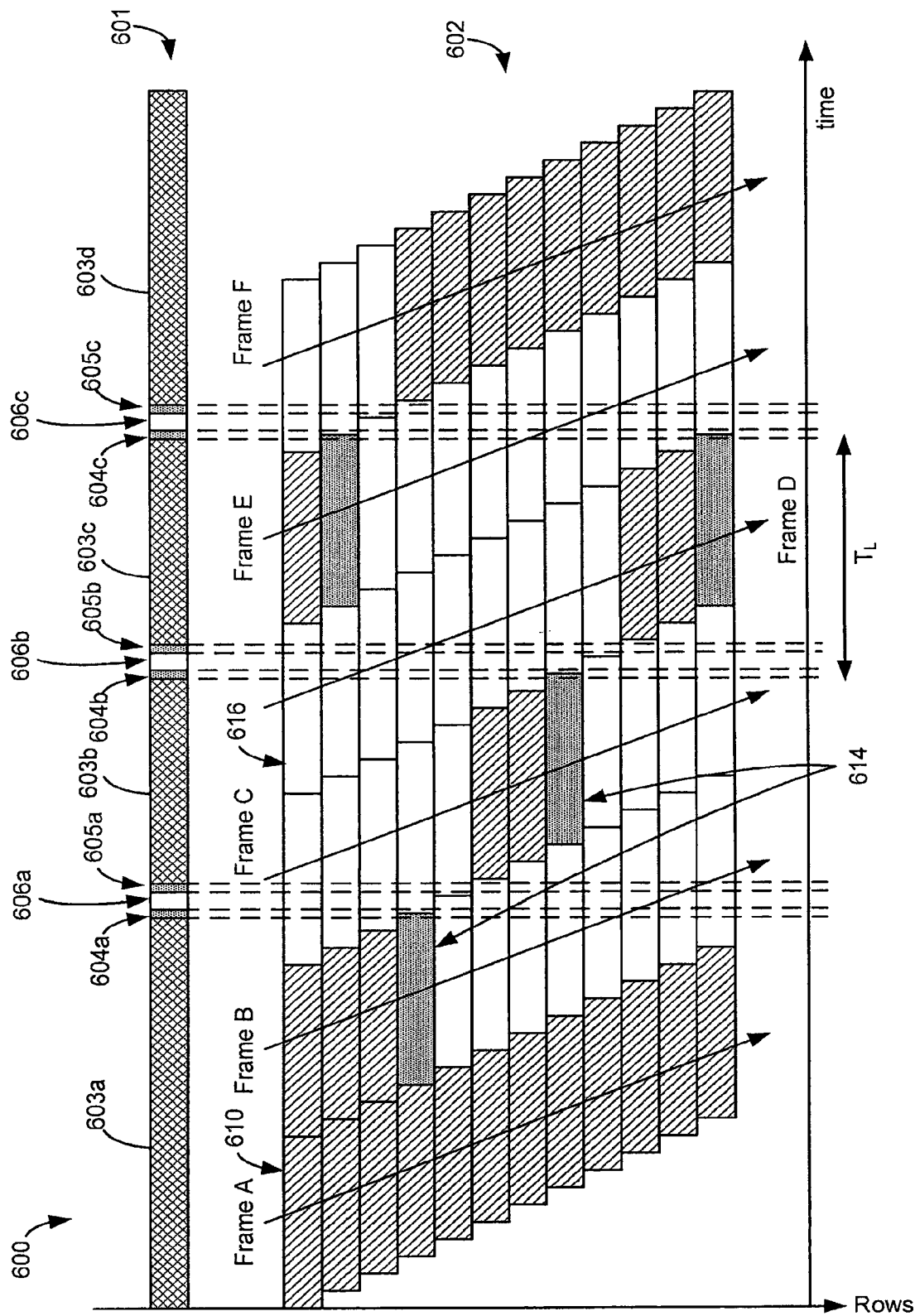
FIG. 6A is a timing diagram illustrating rows with saturated pixels on an imaging device resulting from the operation of a medical device, according to an embodiment.

FIG. 6A is a timing diagram illustrating rows with saturated pixels resulting from the operation of a medical device (e.g., a lithotriptor), according to an embodiment. The timing diagram 600 includes a top portion 601 that illustrates periods when a combustion flash or other like electromagnetic radiation results from a pulse delivered by a medical device, such as the medical device 124 described above with respect to FIG. 1, for example. The timing diagram 600 includes a bottom portion 602 that illustrates multiple video frames associated with a video output from a given imaging device being used with the medical device in a medical procedure (e.g., a lithotripsy procedure), such as the imaging devices 228, 238, and 428 described above with respect to FIGS. 2-4, respectively, for example.

The top portion 601 of the timing diagram 600 includes time periods 603a, 603b, 603c, and 603d (shown with a hatched pattern) during which the medical device does not deliver an electromagnetic radiation pulse to the treatment area or sends a synchronization pulse to the imaging device. The time periods 606a, 606b, and 606c (shown with a white pattern) illustrate periods of time during which a combustion flash or other like electromagnetic radiation results from a pulse delivered by a medical device. The combustion flash can be received by the imaging device as a large pulse or blast of electromagnetic radiation, for example. The time instances 604a and 605a are associated with the start and end, respectively, of a combustion flash or light that occurs during time period 606a. A period $T_L$ between flashes is associated with the frequency of operation ($F_L$) of the medical device.

The bottom portion 602 of the timing diagram 600 illustrates an example of the effects of high levels of electromagnetic radiation (e.g., flashes) on the video frames produced by the imaging device. In this example, the imaging device is operated using a rolling shutter such that each row in a video frame has an exposure start time (e.g., a row reset) that is offset from the exposure start time of an adjacent row in the same frame. Moreover, the frequency of operation of the imaging device (i.e., the frame rate) is substantially the same as the frequency of operation of the medical device ($F_L$).

FIG. 6A shows a frame A at the start (left) of the bottom portion 602 that includes multiple valid rows 610 (shown with a hashed pattern). A valid row 610 is a row that includes a number of valid pixels above a threshold number, for example. A valid pixel can be, for example, a pixel that operates properly (e.g., not defective) and/or is not saturated from being exposed to very high levels of electromagnetic radiation. The frame A occurs within the time period 603a during which the medical device does not deliver electromagnetic radiation to the treatment area or sends a synchronization pulse.

A frame B is shown having its top three rows being valid rows 610. The top three rows of frame B occur within the time period 603a during which a flash or other like deliver electromagnetic radiation associated with the medical device is not received at the imaging device. The end portion of the fourth row (shown with a dotted pattern) of frame B, however, occurs within the time period 606a during which a very high level of electromagnetic radiation is received at the imaging device. The level of electromagnetic radiation is sufficiently high to saturate a large number of pixels in the fourth row of frame B. The fourth row of frame B is corrupted by the saturation of the pixels and is shown as an invalid row 614. The remaining rows of frame B also occur within the time period 606a and are also corrupted by the saturation of pixels that results from the high levels of electromagnetic radiation upon the imaging device. The remaining rows of frame B each can include a large number of saturated pixels and are shown as invalid rows 616 (shown with white pattern). In this embodiment, while the fourth row of frame B is the first row of frame B corrupted by the high levels of electromagnetic radiation upon the imaging device, the imaging device does not reset (i.e., frame B is not prematurely terminated) and the remaining rows of frame B are exposed to the high levels of electromagnetic radiation.

Frames C, D, E, and F in FIG. 6A show the effects of having certain rows occur during the periods of high levels of electromagnetic radiation that can result from the operation of the medical device. For example, frame C includes only two rows that are valid rows 610, frame D includes only two rows that are valid rows 610, frame E includes only one valid row 610, and frame F includes nine valid rows 610.

The example described in FIG. 6A illustrates the effects of operating the medical device at substantially the same frequency as the frame rate of the imaging device. Multiple video frames, in some instances multiple consecutive video frames, can have a very limited number of valid rows because of the pixel saturation effects produced by the operation of the medical device. In this regard, the quality of the video output can be severely affected by the effects that the combustion flashes or like electromagnetic radiation associated with the operation of the medical device have on the imaging device. As a result, a medical practitioner may not be able to use the video output produced by the imaging device to effectively assist in the performance of a medical procedure (e.g., a lithotripsy procedure).

Figure 6B:
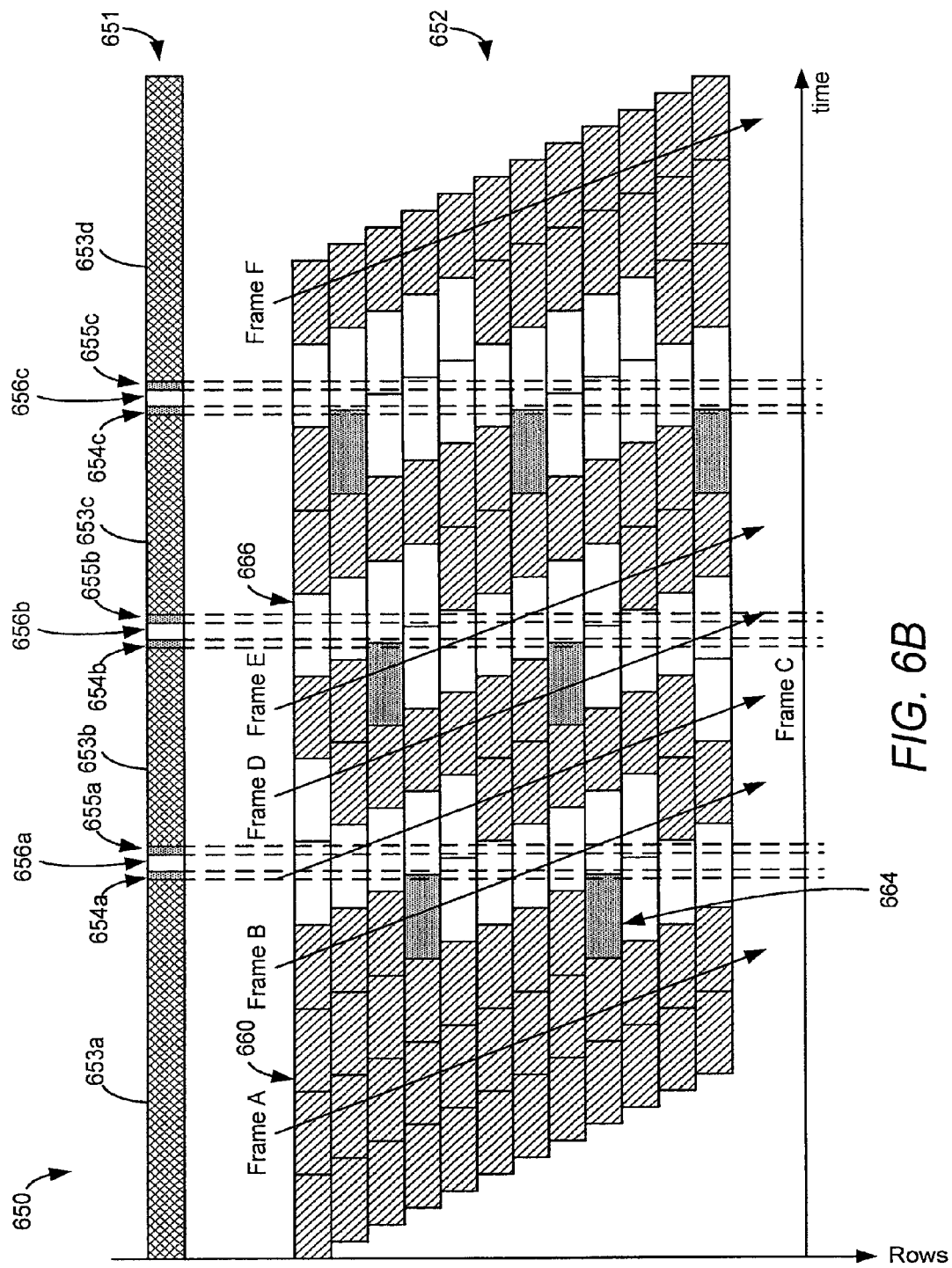
FIG. 6B is a timing diagram illustrating an increased number of valid rows when an imaging device is operated at twice the frequency of operation of a medical device, according to an embodiment.

FIG. 6B is a timing diagram illustrating an increased number of valid rows when an imaging device is operated at is operated, for example, at twice (or higher) the frequency of operation of the medical device, according to an embodiment. The timing diagram 650 includes a top portion 651 that illustrates periods when a combustion flash or other like electromagnetic radiation results from a pulse delivered by a medical device, such as the medical device 124 described above with respect to FIG. 1, for example. The timing diagram 650 includes a bottom portion 652 that illustrates multiple frames associated with a video output from a given imaging device being used in the medical procedure (e.g., a lithotripsy procedure), such as the imaging devices 228, 238, and 428 described above with respect to FIGS. 2-4, respectively, for example. The imaging device operates at a frame rate having a frequency that is at least twice the frequency of operation the medical device. In some embodiments, the frame rate can be less than twice the frequency of the operation of the medical device.

The top portion 651 of the timing diagram 650 includes time periods 653a, 653b, 653c, and 653d (shown with a hatched pattern) during which the medical device does not deliver an electromagnetic radiation pulse to the treatment area or sends a synchronization pulse to the imaging device. The time periods 656a, 656b, and 656c (shown with a white pattern) illustrate periods of time during which a combustion flash or other like electromagnetic radiation results from a pulse delivered by a medical device. For example, the time instances 654a and 655a are associated with the start and end, respectively, of a combustion flash or like electromagnetic radiation that occurs during time period 656a. A period $T_L$ between flashes is associated with the frequency of operation ($F_L$) of the medical device and is substantially the same period as shown in FIG. 6A.

The bottom portion 652 of the timing diagram 650 illustrates an example of the effects of increasing the frame rate of the imaging device to a frequency of at least twice the frequency of operation (e.g., energy or pulse frequency) of the medical device. In this example, the imaging device is operated using a rolling shutter such that each row in a video frame has an exposure start time (e.g., a row reset) that is offset from the exposure start time of an adjacent row in the same video frame.

FIG. 6B shows a frame A at the start (left) of the bottom portion 652 in which all its rows are valid rows 660 (shown with a hashed pattern). The frame A occurs within the time period 653a during which the medical device does not deliver electromagnetic radiation to the treatment area or sends a synchronization pulse. A frame B is shown having its top three rows and its bottom two rows being valid rows 660. The top three rows of frame B occur within the time period 653a during which a flash or other like deliver electromagnetic radiation associated with the medical device is not received at the imaging device. Similarly, the bottom two rows of frame B occur within the time period 653b during which a flash or other like deliver electromagnetic radiation associated with the medical device is not received at the imaging device. The end portion of the fourth row (shown with a dotted pattern) of frame B, however, occurs within the time period 656a during which a very high level of electromagnetic radiation is received at the imaging device. The level of electromagnetic radiation is sufficiently high to saturate a large number of pixels in the fourth row of frame B. The fourth row of frame B is corrupted by the saturation of the pixels and is shown as an invalid row 664. The remaining rows of frame B that occur within the time period 656a are also corrupted by the saturation of pixels that results from the high levels of electromagnetic radiation upon the imaging device and are shown as invalid rows 666 (shown with white pattern).

In contrast to the frames in FIG. 6B, the frames C, D, E, and F in FIG. 6B have a larger number of valid rows as a result of operating the imaging device at a frequency (e.g., frame rate) that is at least twice the operating frequency of the medical device. For example, frame C includes six rows that are valid rows 660, frame D includes six rows that are valid rows 660, frame E includes five valid rows 660, and frame F includes nine valid rows 660.

When the imaging device is operated at twice (or higher) the frequency of operation of the medical device, it is possible to recover the image information with a small loss of signal-to-noise ratio. For example, in one embodiment, adjacent video frames (e.g., frames B, C, and/or D in FIG. 6B) can be added or combined, or at least the valid portions of the adjacent video frames can be added or combined, to substantially replicate the behavior of an imaging device operating at a lower frequency or frame rate. In some embodiments, video frames can be added or combined by adjusting, replacing, and/or modifying rows to produce a video frame at a frequency (e.g., frame rate) that is lower than the frequency of the video frames.

Figure 7:
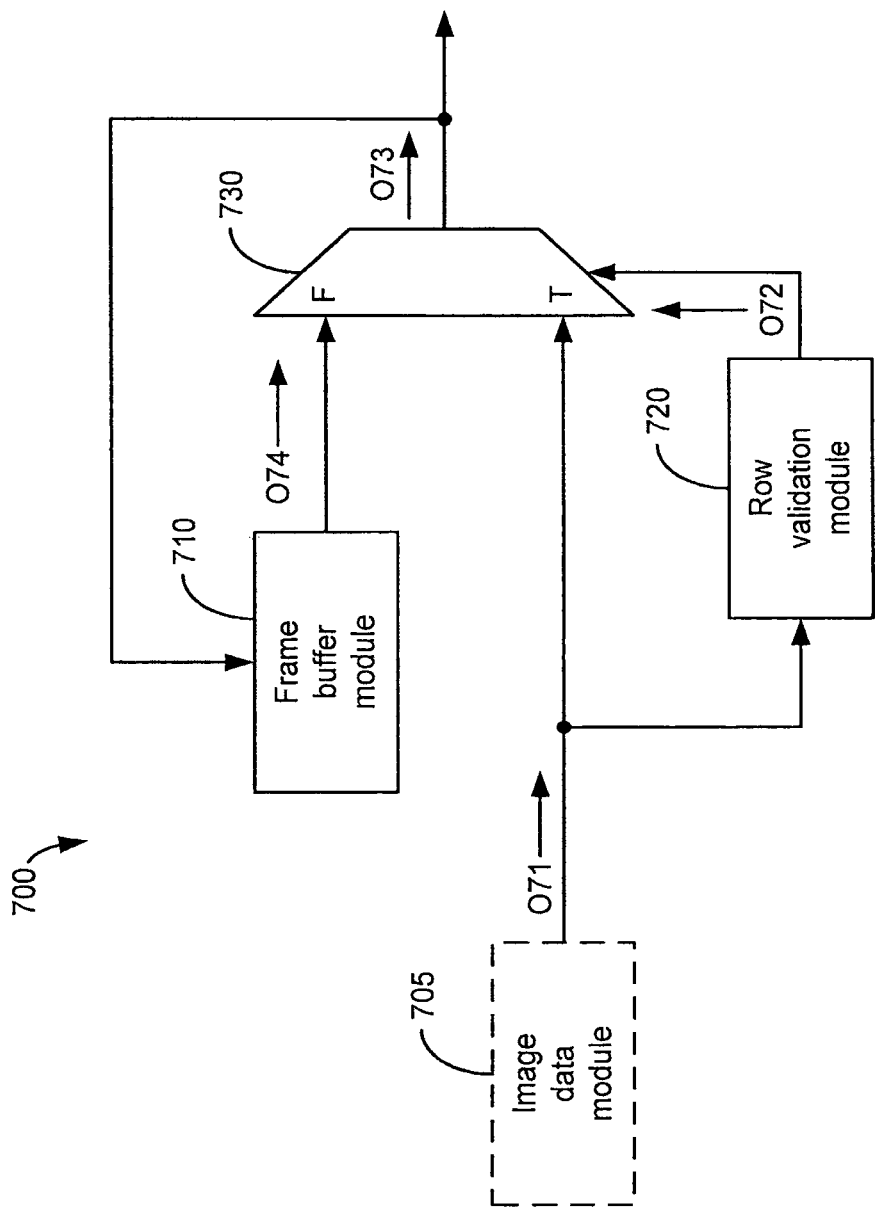
FIG. 7 is a schematic block diagram of a module configured to replace invalid rows, according to an embodiment.

FIG. 7 is a system block diagram of a module 700 configured to replace invalid rows, according to an embodiment. The module 700 includes a row validation module 720, a selector 730, and a frame buffer module 710. In some embodiments, the module 700 can include an image data module 705. In other embodiments, the image data module 705 can be separate from the module 700. In some embodiments, the module 700 can be included in an image processing module such as the image processing modules 220 and 320 described above with respect to FIGS. 2 and 3. In other embodiments, the module 700 can be included in an imaging device configured to having image processing capabilities such as the imaging device 420 described above with respect to FIG. 4. The components of the module 700 can be software-based, or hardware-based and software-based.

The image data module 705 is configured to store video frame information including information associated with one or more rows of a given video frame. The image data module 705 is configured to produce an output O71 that includes information associated with one or more rows from that video frame. The image data module 705 is configured to send the output O71 to the row validation module 720 and to the selector 730.

The row validation module 720 is configured to receive the output O71 from the image data module 705. The row validation module 720 is configured to determine whether a received row is valid or invalid. The validity determination can be based on, for example, a number or percentage of valid pixels in the row, a number or percentage of saturated pixels in a row, and/or a validity of an associated row in one or more video frames related to a time instance before a time instance of the video frame. For example, the validity determination can be based on whether an associated row (e.g., a row in the same location) in a different frame is valid or invalid. The row validation module 720 is configured to produce an output O72 that indicates whether the row received from the image data module 705 is valid or invalid.

The selector 730 is configured to select between the output O71 from the image data module 705 and an output O74 from the frame buffer module 710. The selected output is transferred through the selector 730 to an output O73 produced by the selector 730. When the output O71 from the row validation module 720 indicates that the row received from the image data module 705 is valid, the selector 730 is configured to select the output O71 and transfer the information included in the output O71 to the output O73. The valid row information in the output O73 is also stored in the frame buffer module 710. When the output O71 from the row validation module 720 indicates that the row received from the image data module 705 is invalid, the selector 730 is configured to select the output O74 and transfer the information included in the output O74 to the output O73. In this regard, the invalid row is replaced with a last valid row in the buffer module 710.

The video output produced by a given imaging device can be affected as the combustion flash that is produced at the stone during a medical procedure (e.g., a lithotripsy procedure) can induce a large photo current (i.e., optically-generated current) in the imaging device that can result in changes to the power supply voltage or on-chip bias voltage in the imaging device. These changes in supply voltage can affect the pixel response to electromagnetic radiation (e.g., light response), particularly with respect to a charge or voltage offset (e.g., black level or zero-light level). To compensate or correct for changes that occur to charge or voltage offsets as a result of supply voltage variations, the dark pixels in the imaging device, such as the dark pixels 432 described above with respect to FIG. 4, for example, can be used to determine temporal offset changes based on measurements made on different frames at different instances in time.

Figure 8:
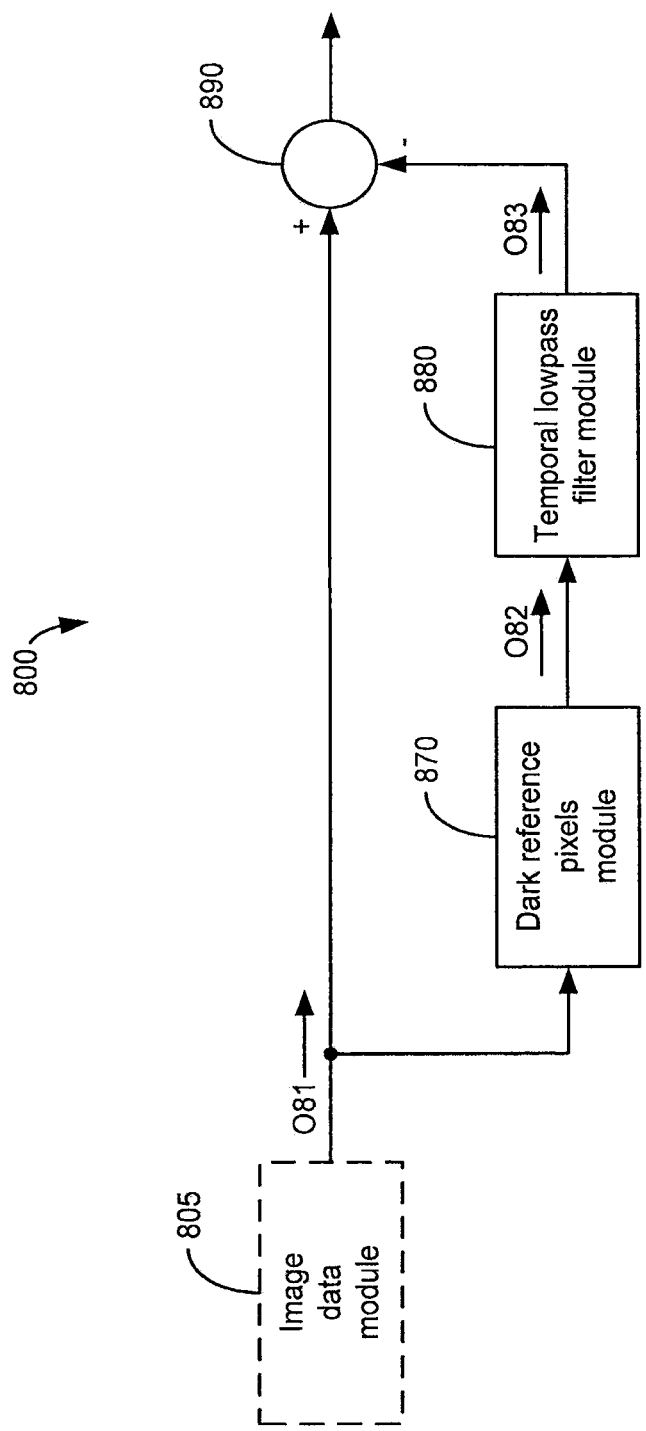
FIG. 8 is a schematic block diagram of a module configured to compensate for changes in pixel offset, according to an embodiment.

FIG. 8 is a schematic block diagram of a module 800 configured to compensate for changes in pixel offset, according to an embodiment. The module 800 includes a dark reference pixels module 870, a temporal lowpass filter module 880, and an adder 890. In some embodiments, the module 800 can include an image data module 805. In other embodiments, the image data module 805 can be separate from the module 800. In some embodiments, the module 800 can be included in an image processing module such as the image processing modules 220 and 320 described above with respect to FIGS. 2 and 3. In other embodiments, the module 800 can be included in an imaging device configured to having image processing capabilities such as the imaging device 420 described above with respect to FIG. 4. The components of the module 800 can be software-based or hardware-based and software-based.

The image data module 805 is configured to store video frame information including information associated with one or more rows of a given video frame. The image data module 805 can include dark pixel information associated with the video frame. The image data module 805 is configured to produce an output O81 that includes information associated with one or more rows from that video frame and/or dark pixel information associated with that video frame. The image data module 805 is configured to send the video frame information to the adder 890 and the dark pixel information to the dark reference pixels module 870.

The dark reference pixels module 870 is configured to receive dark pixel information associated with one or more rows of a video frame. The dark reference pixels module 870 is configured to collect, organize, and/or process the dark pixel information. In some embodiments, the dark reference pixels module 870 can include a buffer (not shown) to store dark pixel information associated with one or more video frames. The dark reference pixels module 870 is configured to produce an output O82 that includes information associated with the dark pixel information received and/or processed by the dark reference pixels module 870.

The temporal lowpass filter module 880 is configured to receive the output O82 from the dark reference pixels module 870. The temporal lowpass filet module 880 is configured to temporally and/or spatially filter the dark pixel information associated with the video frame or the dark pixel information associated with a video frame at a time before the time of the video frame. For example, the filtering that occurs in the temporal lowpass filet module 880 can be based on dark pixel information from a current video frame and/or from one or more previous video frames. The filtering provided by the temporal lowpass filter module 880 can be used to prevent or reduce normal levels of noise in the imaging device from disrupting the image in the video output, particularly when large gains are to be applied subsequently to the information associated with the video frame. The temporal lowpass filter module 880 is configured to produce an output O83 that includes the filtered dark pixel information. The adder 890 is configured to subtract the filtered dark pixel in the output O83 from the video frame information in the output O81 from the image data module 805. By subtracting the filtered dark pixel information from the video frame information, the module 800 can compensate for the changes in charge or voltage offset produced by the imaging device from the variations in supply voltage that result from the combustion flash associated with the operation of the medical device.

Figure 9:
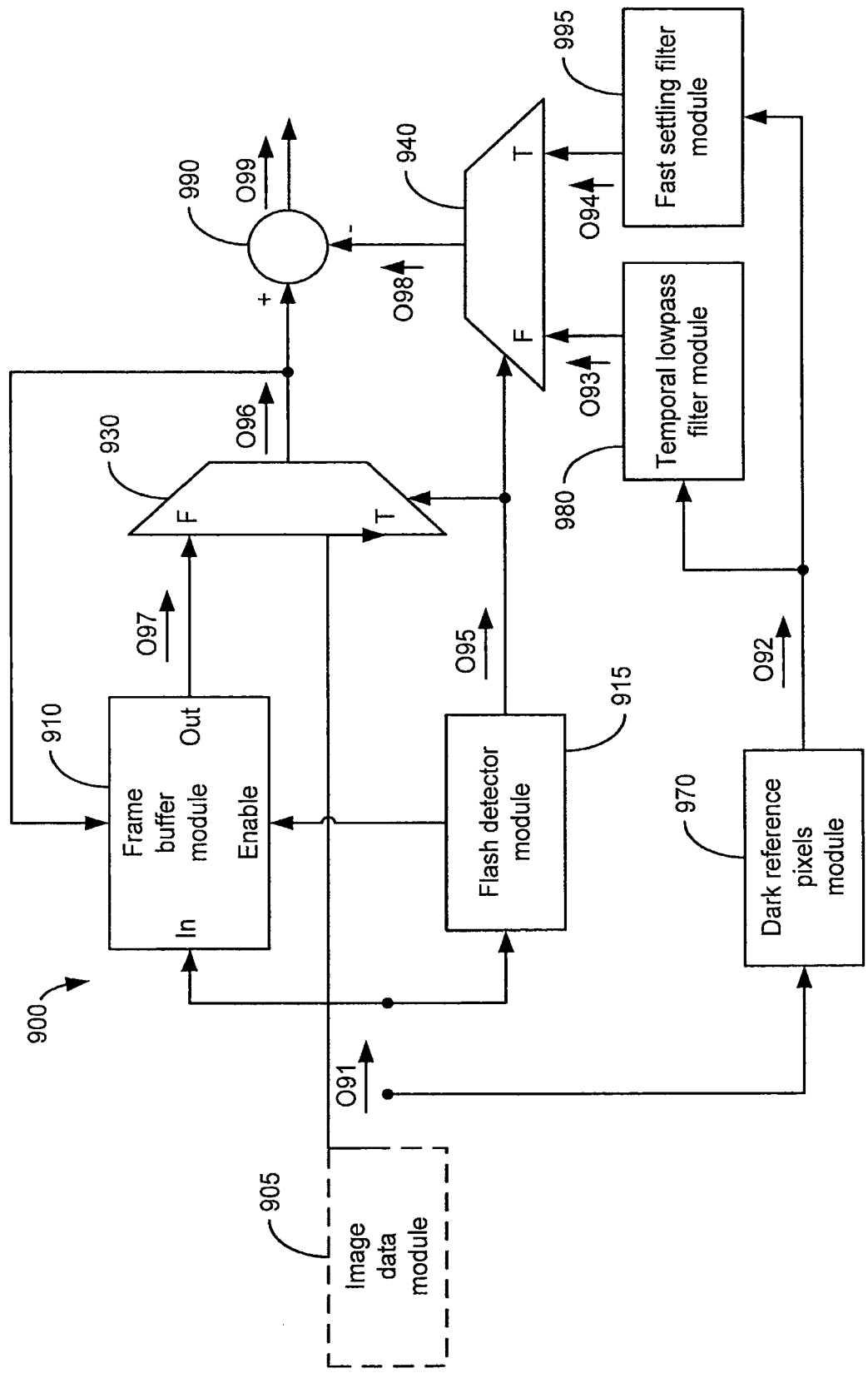
FIG. 9 is a schematic block diagram of a module configured to replace invalid rows and to compensate for changes in pixel offset, according to an embodiment.

FIG. 9 is a schematic block diagram of a module 900 configured to replace invalid rows and compensate for changes in pixel offset, according to an embodiment. The module 900 includes a dark reference pixels module 970, a temporal lowpass filter module 980, a fast-settling filter module 995, a selector 940, a frame buffer module 910, a flash detector module 915 (e.g., a lithotripsy flash detector module), a selector 930, and an adder 990. In some embodiments, the module 900 can include an image data module 905. In other embodiments, the image data module 905 can be separate from the module 900. In some embodiments, the module 900 can be included in an image processing module such as the image processing modules 220 and 320 described above with respect to FIGS. 2 and 3. In other embodiments, the module 900 can be included in an imaging device configured to having image processing capabilities such as the imaging device 420 described above with respect to FIG. 4. The components of the module 900 can be software-based or hardware-based and software-based.

The image data module 905 is configured to store video frame information including information associated with one or more rows of a given video frame. The image data module 905 can include dark pixel information associated with the video frame. The image data module 905 is configured to produce an output O91 that includes information associated with one or more rows from that video frame and/or dark pixel information associated with that video frame. The image data module 905 is configured to send the video frame information in output O91 to the selector 930, the frame buffer module 910, and/or the flash detector module 915. The image data module 905 is configured to send dark pixel information in output O91 to the dark reference pixels module 970.

The flash detector module 915 is configured to determine when a received row or rows from a video frame are valid or invalid. The flash detector module 915 is configured to determine when a flash or like electromagnetic radiation occurs associated with the medical device based on, for example, the validity of rows from the video frame. The flash detector module 915 is configured to produce an output O95 that indicates whether the row received from the image data module 705 is valid or invalid. The flash detector module 915 is configured to enable the storage of valid rows on the frame buffer module 910 when a row is determined to be a valid row.

The selector 930 is configured to select between the output O91 from the image data module 905 and an output O97 from the frame buffer module 910. The selected output is transferred through the selector 930 to an output O96 produced by the selector 930. When the output O91 from the flash detector 915 indicates that the row received from the image data module 905 is valid, the selector 930 is configured to select the output O91 and transfer the information included in the output O91 to the output O96. The valid row information in the output O96 is also stored in the frame buffer module 910. When the output O91 from the flash detector 915 indicates that the row received from the image data module 905 is invalid, the selector 930 is configured to select the output O97 and transfer the information included in the output O97 to the output O96. The frame buffer module 910 is configured to include in the output O96 information associated with a valid row (e.g., a valid row from a previous frame) that can be used to replace or correct at least a portion of the received row deemed to be invalid by the flash detector 915. For example, the invalid row can be replaced with a last valid row stored in the frame buffer module 910.

The dark reference pixels module 970 and the temporal lowpass filter module 980 can be similar to the dark reference pixels module 870 and the temporal lowpass filter module 880 described above with respect to FIG. 8, respectively. The dark reference pixels module 970 is configured to produce an output O92 that includes information associated with the dark pixel information received and/or processed by the dark reference pixels module 970. The output O92 is received by the temporal lowpass filter module 980 and the fast-settling filter module 995. The fast-settling filter module 995 is configured to temporally and/or spatially filter the dark pixel information associated with the video frame or the dark pixel information associated with a video frame at a time (e.g., relative time) before the time of the video frame.

The selector 940 is configured to select between the output O93 from the temporal lowpass filter module 980 and an output O94 from the fast-settling filter module 995. The selected output is transferred through the selector 940 to an output O98 produced by the selector 940. When the output O91 from the flash detector 915 indicates that the row received from the image data module 905 is valid, the selector 940 is configured to select the output O93 and transfer the information included in the output O93 to the output O98. When the output O91 from the flash detector 915 indicates that the row received from the image data module 905 is invalid, or that multiple rows received from the image data module 905 are invalid, the selector 940 is configured to select the output O94 and transfer the information included in the output O94 to the output O98. In this regard, when a predetermined number of rows received from the image data module 905 are invalid, it is desirable that the fast-settling filter module 995 be selected. In a fast-settling mode, data can be buffered in the frame buffer module 910 until a next valid row is received from the image data module 905. The dark reference pixel information is collected until a sufficiently large information sample is obtained to cancel out or compensate for a large portion of the noise that is part of individual samples of the dark reference pixel information. The compensated dark reference pixel information can be averaged to determine a charge or voltage offset to be subtracted from the video data information.

The adder 990 is configured to subtract the dark pixel information (e.g., offset information) in the output O98 from the selector 940 from the video frame information in the output O96 from the selector O93 to produce an output O99. By subtracting the dark pixel information from the video frame information, the module 900 can compensate for invalid rows and for the changes in charge or voltage offset produced by the imaging device from the variations in supply voltage that result from the combustion flash associated with the operation of the medical device.

Figure 10:
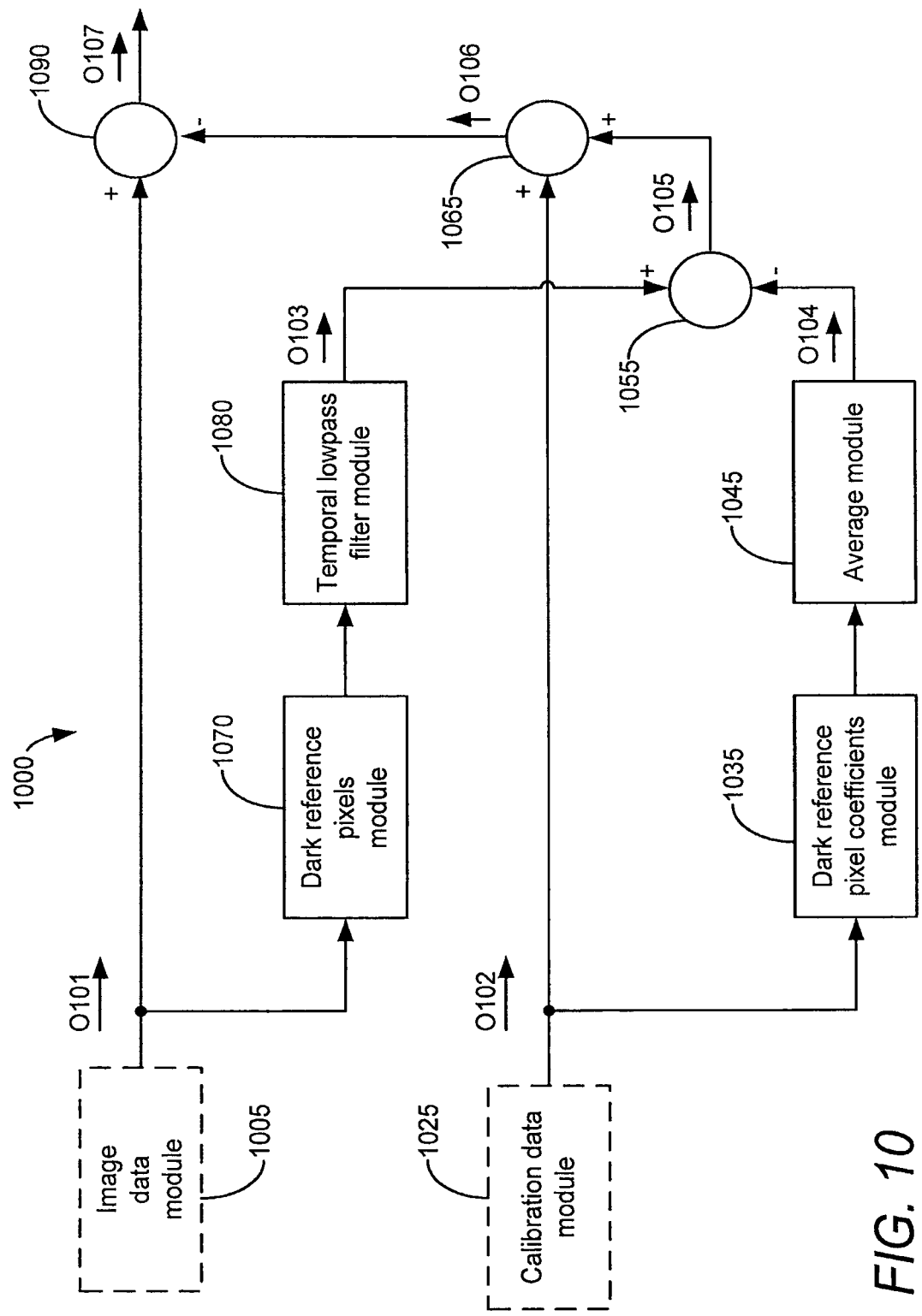
FIG. 10 is a schematic block diagram of a module configured to compensate for changes in pixel offset, according to another embodiment.

FIG. 10 is a schematic block diagram of a module 1000 configured to compensate for changes in pixel offset, according to another embodiment. The module 1000 includes a dark pixel coefficients module 1035, an average module 45, a dark reference pixels module 1070, a temporal lowpass filter module 80, and adders 1055, 65, and 1090. In some embodiments, the module 1000 can include an image data module 1005 and/or the calibration data module 1025. In other embodiments, the image data module 1005 and/or the calibration data module 1025 can be separate from the module 1000. In some embodiments, the module 100 can be included in an image processing module such as the image processing modules 220 and 320 described above with respect to FIGS. 2 and 3. In other embodiments, the module 1000 can be included in an imaging device configured to having image processing capabilities such as the imaging device 420 described above with respect to FIG. 4. The components of the module 1000 can be software-based or hardware-based and software-based.

The image data module 1005, the dark reference pixels module 1070, and the temporal lowpass filter module 80 are similar to the image data module 805, the dark reference pixels module 870, and the temporal lowpass filter module 880 described above with respect to FIG. 8. In this regard, the output O101 from the image data module 1005 includes information associated with one or more rows from that video frame and/or dark pixel information associated with that video frame. The temporal lowpass tilter module 80 is configured to produce an output O103 that that includes filtered dark pixel information.

In this embodiment, an offset for each pixel in a video frame can be individually corrected or compensated to account for normal variations in leakage (dark) current and/or other offsets (e.g., source-follower threshold voltage) that occur across a pixel array as a result of the manufacturing process.

The calibration data module 1025 is configured to store information associated with offset correction coefficients of a given imaging device. In one example, the offset correction coefficients can include a charge or voltage offset associated with each dark pixel in the array of the imaging device obtained or determined during a manufacturing or system calibration operation. The calibration data module 1025 is configured to produce an output O102 that includes the information associated with the offset correction coefficients. The dark reference pixel coefficients module 1035 is configured to process the information associated with offset correction coefficients. The average module 1045 is configured to average the processed information associated with offset correction coefficients from the dark reference pixel coefficients module 1035. The average module 1045 is configured to produce an output O103 that includes averaged offset correction coefficients information.

The adder 1055 is configured to subtract the output O104 from the average module 1045 from the output O103 from the temporal lowpass filter module 1080 to produce an output O105. The adder 65 is configured to add the output O105 from the adder 1055 and the output O2 from the calibration data module 1025 to produce an output O6. The adder 1090 is configured to subtract the output O106 from the adder 1065 from the output O101 from the image data module 1005 to produce an output O107. The output O107 includes video frame information that has been adjusted to compensate for offset differences between calibration conditions and operating conditions.

Figure 11:
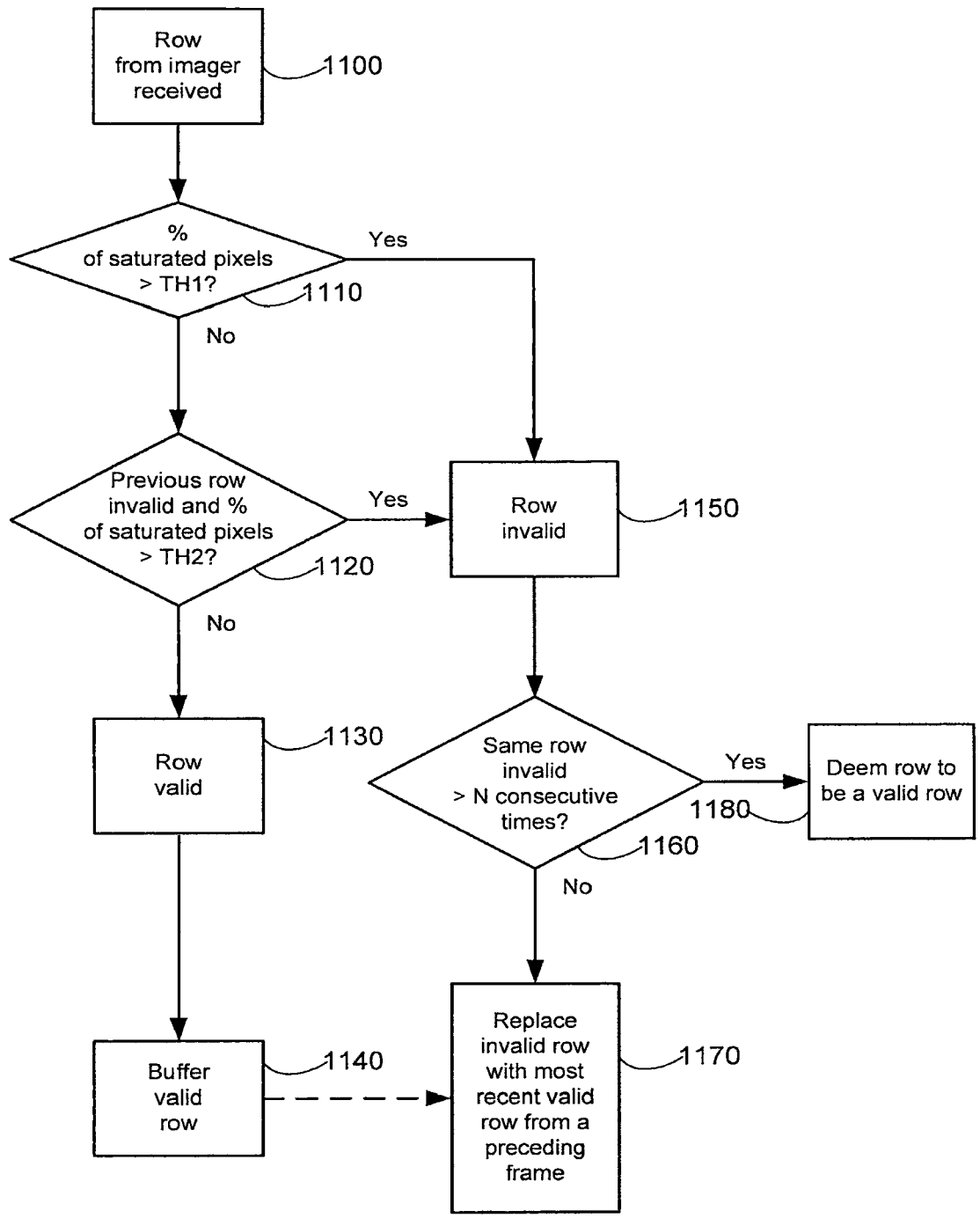
FIG. 11 is a flow chart illustrating a method for replacing invalid rows, according to an embodiment.

FIG. 11 is a flow chart illustrating a method for replacing invalid rows, according to an embodiment. At 1100, a row associated with a given frame is received from an imaging device (e.g., an image sensor). At 1110, the number of saturated pixels in the received row is determined. When the number (or percentage) of saturated pixels is above a first predetermined threshold number (or threshold percentage), TH1, the process proceeds to 1150 where the received row is determined or deemed to be an invalid row. When the number (or percentage) of saturated pixels is below or equal to the first predetermined threshold number (or threshold percentage), TH1, the process proceeds to 1120. In one example, a received row can be deemed to be invalid when the percentage of saturated pixels is above 50% of the total number of pixels in the row.

At 1120, when a previous row in the same frame that includes the received row is an invalid row and the number (or percentage) of saturated pixels in the current row is above a second predetermined threshold number (or threshold percentage), TH2, where TH2 is lower than TH1, then the process proceeds to 1150 where the received row is determined or deemed to be an invalid row. Otherwise, the process proceeds to 1130 where the received row is determined or deemed to be a valid row. A prior invalid row can include an immediately prior row that was deemed invalid or a row within a predetermined number of prior rows of the frame that includes the received row that was deemed invalid. After 1130, at 1140, the received row is deemed to be a valid row can be stored in a buffer.

After 1150, at 1160, when the same row as the received row in multiple consecutive frames (e.g., more than N consecutive frames) has been deemed to be an invalid row, the process can proceed to 1180 where the received row that was deemed to be an invalid row at 1150 is now deemed to be a valid row. Otherwise, the process can proceed to 1170 where the received row deemed to be an invalid row is replaced in the frame including the received row with a valid row from a frame at a time (e.g., relative time) earlier than the time of the frame that includes the received row. For example, the valid row to be used to replace the received row deemed to be an invalid row can come from the buffer at 1140.

The correction operation described with respect to 1160 and 1180 above can be used to prevent an area of an image in the video output from being static for a substantial period of time (e.g., 100 milliseconds) as a result of consecutive invalid rows in the same location. Such a long period of time can make the identification and processing of invalid rows more visible to a human observer (e.g., medical practitioner) and, sometimes, more objectionable than the artifacts sought to be addressed. In one example, when operating at a frame rate of 30 frames-per-second (fps), the number N of consecutive frames in 1160 can be set to, for example, three consecutive replacements before an invalid row is to be deemed valid. The selection of the number (N) of consecutive frames in 1160 can depend on various factors, including apparent latency and/or the likelihood or probability of false or misclassification of a row as an invalid row.

Figure 12:
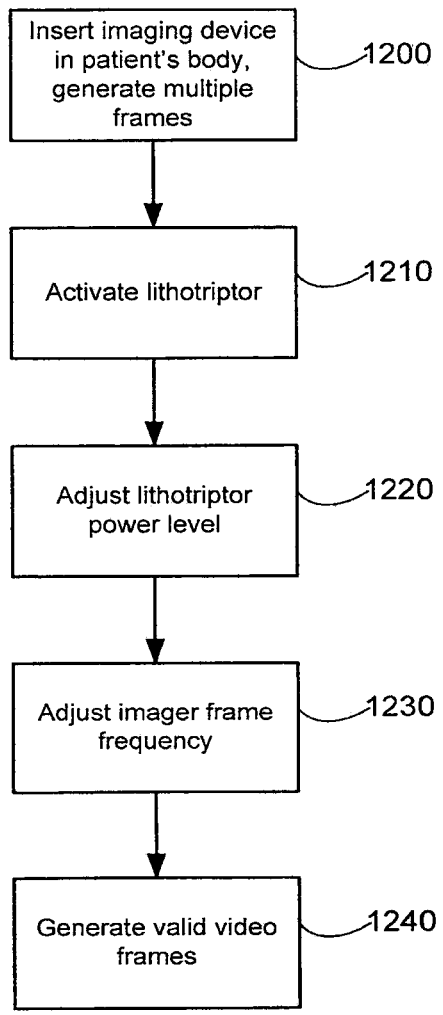
FIG. 12 is a flow chart illustrating a method forming an imaging device proximate to a medical device, according to an embodiment.

FIG. 12 is a flow chart illustrating a method for using an imaging device proximate to a medical device (e.g., a lithotriptor), according to an embodiment. At step 1200, an imaging device, such as the imaging devices 228, 328, and 428 described above with respect to FIGS. 2-4, is inserted into a patient's body. At 1210, after the inserting at 1200, a medical device, such as the medical device 124 described above with respect to FIG. 1, for example, is activated to transmit (e.g., emit) an electromagnetic energy or a synchronization pulse to the patient's body. The imaging device generates multiple frames (e.g., video frames) at a frame frequency of, for example, at least twice a frequency of operation (e.g., energy or pulse frequency) of the medical device. The imaging device terminates at least a current frame from the multiple frames in response to at least one of a synchronization pulse from the medical device or an electromagnetic energy associated with the medical device. A start or reset time of each row in each frame from the multiple frames is offset from a start or reset time of an adjacent row in that same frame.

At 1220, a power level of the electromagnetic radiation or energy transmitted (e.g., emitted) to the patient's body from the medical device is adjusted. In one example, the power level is adjusted by a medical practitioner. In another example, the power level is adjusted to a predetermined level by, for example, a medical device such as the control module 210 described above with respect to FIG. 2. At 1230, the frame frequency or frame rate of the multiple frames from the imaging device is adjusted. At 1240, a frame from the multiple frames can be determined to be a valid frame. In some embodiments, the valid frame can result from adding or combining valid portions of two or more frames from the multiple frames. Multiple valid frames can be generated that include the frame determined to be a valid frame. The multiple valid frames have a frame frequency that is lower than the frame frequency of the multiple frames.

While various embodiments have been described above, it should be understood that they have been presented by way of example only, and not limitation. For example, the imaging system described herein can include various combinations and/or sub-combinations of the components and/or features of the different embodiments described. Embodiments of the image processing module can be provided without the imaging device described herein. In other embodiments, components and/or features of the image processing module can be included in the imaging device. Although described with reference to use with a medical device and related to medical procedures (e.g., lithotripsy procedures), it should be understood that the imaging device and the image processing module, as well as the methods of using the imaging device and the image processing modules can be used in the treatment of other conditions.

Some embodiments may include a processor and a related processor-readable medium having instructions or computer code thereon for performing various processor-implemented operations. Such processors may be implemented as hardware modules such as embedded microprocessors, microprocessors as part of a computer system, Application-Specific Integrated Circuits ("ASICs"), and Programmable Logic Devices ("PLDs"). Such processors may also be implemented as one or more software modules in programming languages as Java, C++, C, assembly, a hardware description language, or any other suitable programming language.

A processor according to some embodiments may include media and computer code (also can be referred to as code) specially designed and constructed for the specific purpose or purposes. Examples of processor-readable media include, but are not limited to: magnetic storage media, such as hard disks, floppy disks, and magnetic tape; optical storage media, such as Compact Disc/Digital Video Discs ("CD/DVDs"), Compact Disc-Read Only Memories ("CD-ROMs"), and holographic devices; and magneto-optical storage media, such as optical disks and read-only memory ("ROM") and random-access memory ("RAM") devices. Examples of computer code include, but are not limited to, micro-code or micro-instructions, machine instructions, such as produced by a compiler, and files containing higher-level instructions that are executed by a computer using an interpreter. For example, an embodiment may be implemented using Java, C++, or other object-oriented programming language and development tools. Additional examples of computer code include, but are not limited to, control signals, encrypted code, and compressed code.

The many features and advantages of the present disclosure are apparent from the detailed specification, and thus, it is intended by the appended claims to cover all such features and advantages of the present disclosure which fall within the true spirit and scope of the present disclosure. Further, since numerous modifications and variations will readily occur to those skilled in the art, it is not desired to limit the present disclosure to the exact construction and operation illustrated and described, and accordingly, all suitable modifications and equivalents may be resorted to, falling within the scope of the present disclosure.

What is claimed is:

1. An apparatus, comprising:
an imager configured to generate a plurality of frames at a frame frequency greater than an electromagnetic energy emission pulse frequency of a medical device, each frame of the plurality of frames including a first plurality of rows;
an electronic shutter module configured to offset a start time of each row of the first plurality of rows in each frame from the plurality of frames from a start time of an adjacent row in that same frame; and
an image processing module configured to generate a plurality of valid frames based on at least a portion of the plurality of frames generated by the imager, the plurality of valid frames having a frame frequency lower than the frame frequency of the plurality of frames.

2. The apparatus of claim 1, wherein the electronic shutter module terminates a current frame from the plurality of frames in response to at least one of a synchronization pulse from the medical device and an electromagnetic energy associated with the medical device.

3. The apparatus of claim 1, wherein the imager is a solid-state imager having an addressable pixel array including a second plurality of rows, each row of the second plurality of rows being associated with a row from the first plurality of rows in a frame from the plurality of frames.

4. The apparatus of claim 1, wherein a valid portion of a frame from the plurality of frames includes at least one valid row and is included in a valid frame from the plurality of valid frames.

5. The apparatus of claim 1, wherein the image processing module includes a temporal filter configured to combine a valid portion of at least two adjacent frames from the plurality of frames to produce a valid frame from the plurality of valid frames.

6. The apparatus of claim 1, wherein the imager is configured to read out an initial frame from the plurality of frames in response to at least one of a power-on reset being complete and a synchronization signal from the medical device.

7. The apparatus of claim 1, wherein a first frame from the plurality of frames is before a second frame from the plurality of frames, and wherein the electronic shutter module is configured to reset to a start of the second frame after the first frame is terminated in response to at least one of a synchronization pulse from the medical device and an electromagnetic energy associated with the medical device.

8. The apparatus of claim 1, wherein a valid frame from the plurality of valid frames includes at least one valid row, the at least one valid row having a number of valid pixels above a predetermined threshold number.

9. The apparatus of claim 1, wherein a first frame from the plurality of frames is before a second frame from the plurality of frames, and wherein the image processing module is configured to replace an invalid portion of the second frame with an associated valid portion from the first frame.

10. The apparatus of claim 1, wherein the image processing module includes a buffer configured to store a valid portion of at least one frame from the plurality of frames.

11. The apparatus of claim 1, wherein the image processing module is configured to adjust an illumination value associated with a pixel in a valid frame from the plurality of valid frames based on at least one of a dark reference pixel information received from the imager and a calibration information stored in the image processing module.

12. The apparatus of claim 1, wherein the image processing module includes a temporal low-pass filter module configured to produce an output based on a dark reference pixel information received from the imager, and wherein the image processing module is configured to adjust an illumination value associated with a pixel in a valid frame from the plurality of valid frames based on the output from the temporal low-pass filter.

13. The apparatus of claim 1, wherein the image processing module includes a fast-settling filter module configured to produce an output based on a dark reference pixel information received from the imager, wherein the fast-settling filter module is actuated in response to at least one of a synchronization pulse from the medical device and an electromagnetic energy associated with the medical device, and wherein the image processing module is configured to adjust an illumination value associated with a pixel in a valid frame from the plurality of valid frames based on the output from the fast-settling filter.

14. The apparatus of claim 1, wherein the apparatus includes an endoscope.

15. A method, comprising:
generating a plurality of video frames with an imager, the plurality of video frames including at least a first video frame and a second video frame;
determining whether a row in a video frame from the plurality of video frames is an invalid row in response to receiving electromagnetic energy;
replacing at least one invalid row in the second video frame with an associated valid row from the first video frame to produce a valid video frame; and
generating a plurality of valid video frames, the plurality of valid video frames having a frame frequency lower than a frame frequency of the plurality of video frames generated by the imager.

16. The method of claim 15, further comprising generating the plurality of video frames at a first frequency, the first frequency being greater than an electromagnetic energy emission pulse frequency of a medical device.

17. The method of claim 15, wherein a row in the second video frame is invalid when an associated row in the first video frame is invalid and a number of valid pixels in the row in the second video frame is below a predetermined threshold number.

18. The method of claim 15, further comprising deeming an invalid row to be a valid row after the invalid row has been replaced in a predetermined number of consecutive video frames from the plurality of video frames.

19. A method, comprising:
inserting an imager into a body of a patient;
activating a medical device to transmit an electromagnetic energy to the body of the patient;
generating a plurality of frames at a frame frequency greater than an electromagnetic energy emission pulse frequency of the medical device, wherein the imager is configured to terminate at least a frame from the plurality of frames in response to at least one of a synchronization pulse from the medical device and an electromagnetic energy associated with the medical device; and
offsetting a start time of each row in each frame from the plurality of frames from a start time of an adjacent row in that same frame.

20. The method of claim 19, further comprising:
adjusting a power level of the electromagnetic energy transmitted to the body of the patient from the medical device;
adjusting the frame frequency of the plurality of frames;
determining whether a frame from the plurality of frames is a first valid frame; and
generating a plurality of valid frames including the first valid frame, the plurality of valid frames having a frame frequency lower than a frame frequency of the plurality of frames.

* * * * *